US010744336B2

(12) United States Patent
Sekino et al.

(10) Patent No.: US 10,744,336 B2
(45) Date of Patent: Aug. 18, 2020

(54) COIL, AND MAGNETIC STIMULATION DEVICE USING THE COIL

(71) Applicant: THE UNIVERSITY OF TOKYO, Tokyo (JP)

(72) Inventors: Masaki Sekino, Tokyo (JP); Keita Yamamoto, Tokyo (JP); Yuta Kawasaki, Tokyo (JP)

(73) Assignee: THE UNIVERSITY OF TOKYO, Tokyo (JP)

(*) Notice: Subject to any disclaimer, the term of this patent is extended or adjusted under 35 U.S.C. 154(b) by 224 days.

(21) Appl. No.: 15/763,917

(22) PCT Filed: Feb. 28, 2017

(86) PCT No.: PCT/JP2017/007641
§ 371 (c)(1),
(2) Date: Mar. 28, 2018

(87) PCT Pub. No.: WO2017/150490
PCT Pub. Date: Sep. 8, 2017

(65) Prior Publication Data
US 2018/0280711 A1 Oct. 4, 2018

(30) Foreign Application Priority Data

Mar. 4, 2016 (JP) .................. 2016-042364

(51) Int. Cl.
*A61N 2/00* (2006.01)
*A61N 2/02* (2006.01)

(52) U.S. Cl.
CPC .............. *A61N 2/006* (2013.01); *A61N 2/02* (2013.01)

(58) Field of Classification Search
CPC .................... A61N 2/006; A61N 2/02
See application file for complete search history.

(56) References Cited

U.S. PATENT DOCUMENTS 4,994,015 A * 2/1991 Cadwell ................ A61N 2/006
335/299
2012/0157752 A1 6/2012 Nishikawa et al.
(Continued)

FOREIGN PATENT DOCUMENTS

EP   2 982 411 A1    2/2016
JP   2012-125546 A   7/2012
(Continued)

OTHER PUBLICATIONS

Yu Miyawaki et al., "Tesshin no Riyo ni yoru Henshin Hachinoji Coil no Jiki Shigeki Koritsu no Kojo (Improved efficiency of eccentric eight-figure stimulator coil with iron core)", Dai 30 Kai Japan Biomagnetism and Bioelectromagnetics Society Taikai Ronbunshu, 2015, pp. 172-173, vol. 28, No. 1.
(Continued)

*Primary Examiner* — Christine H Matthews
*Assistant Examiner* — Joshua Daryl D Lannu
(74) *Attorney, Agent, or Firm* — Sughrue Mion, PLLC

(57) ABSTRACT

A coil has 1st to Nth turns. The 1st to Nth turns respectively provided with actuation parts for current in one direction to flow, and connection parts for current in the opposite direction to the one direction to flow. The plurality of actuation parts are arranged substantially parallel to each other, and are arranged along a surface of an object or a surface that approximates to the surface of the object. A plurality of connection parts are arranged within a space in which the connection parts do not face the surface of the object over the actuation parts of the 1st to Nth turns, and the connection parts are positioned at the sides with respect to the extension direction of the actuation parts.

13 Claims, 33 Drawing Sheets

(56) References Cited

U.S. PATENT DOCUMENTS

| | | | |
|---|---|---|---|
| 2013/0317281 A1 | 11/2013 | Schneider et al. | |
| 2014/0235927 A1* | 8/2014 | Zangen | A61N 2/02 600/13 |
| 2014/0235928 A1* | 8/2014 | Zangen | A61N 2/02 600/14 |
| 2015/0133718 A1 | 5/2015 | Schneider et al. | |
| 2015/0196772 A1* | 7/2015 | Ghiron | A61N 2/006 600/14 |
| 2016/0346562 A1 | 12/2016 | Saitoh et al. | |

FOREIGN PATENT DOCUMENTS

| | | |
|---|---|---|
| WO | 2010/147064 A1 | 12/2010 |
| WO | 2015/122506 A1 | 8/2015 |

OTHER PUBLICATIONS

International Search Report for PCT/JP2017/007641, dated May 9, 2017.
Communication dated Aug. 9, 2019 from European Patent Office in counterpart EP Application No. 17759956.0.

* cited by examiner

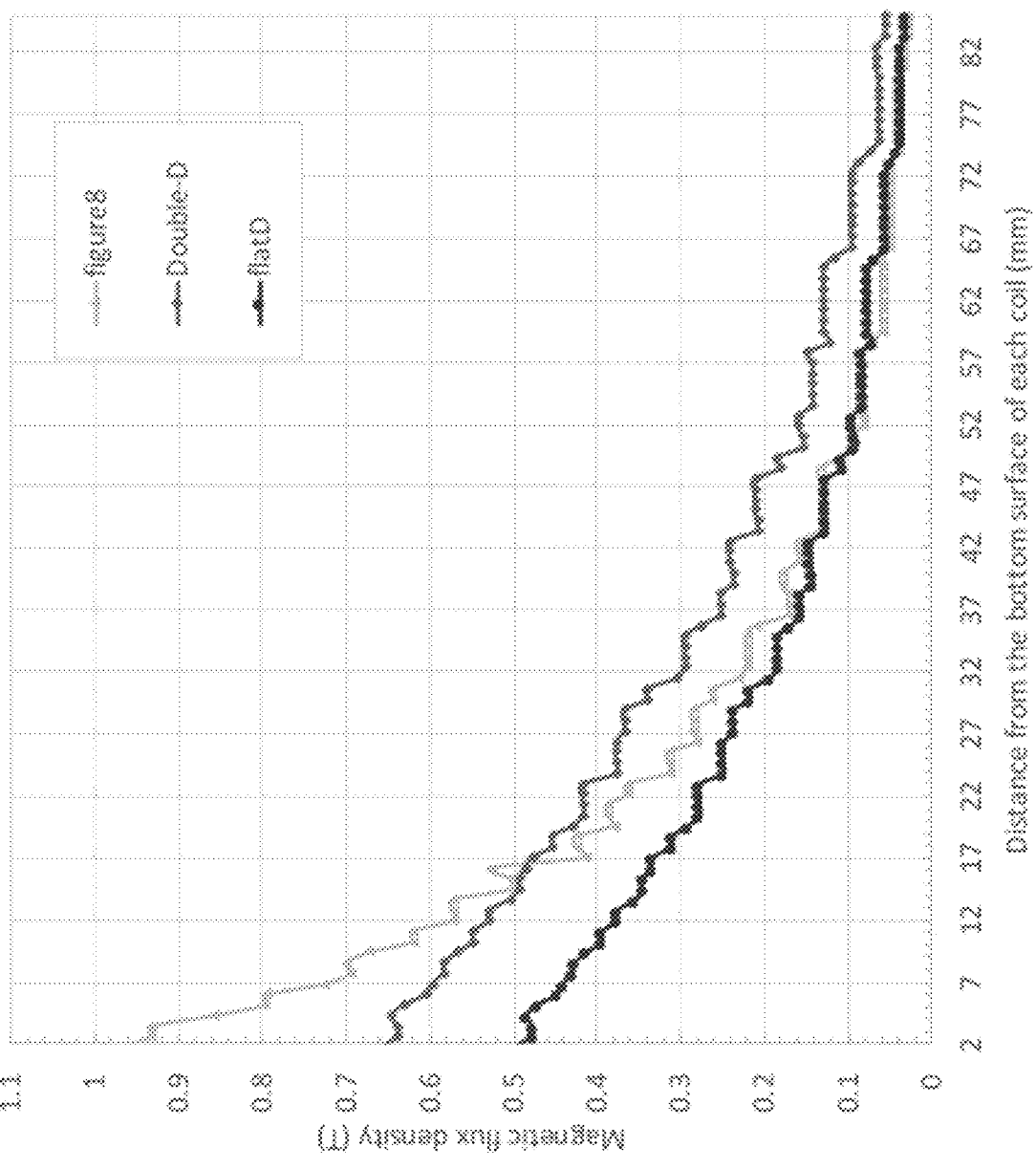

COIL, AND MAGNETIC STIMULATION DEVICE USING THE COIL

This application is a National Stage of International Application No. PCT/JP2017/007641 filed Feb. 28, 2017, claiming priority based on Japanese Patent Application No. 2016-042364 filed Mar. 4, 2016.

TECHNICAL FIELD

The present invention relates to a coil, and to a magnetic stimulation device that uses this coil.

BACKGROUND ART

Transcranial Magnetic Stimulation (TMS) is a method of causing current flow within the brain by electromagnetic induction, and stimulating neurons. According to this method, as shown in FIG. 1 to FIG. 3, by applying an alternating current or a given current waveform to a stimulation coil that has been placed above a person's scalp, a variable magnetic field is generated, and the effect of that variable magnetic field is to induce, within the brain, eddy current in a reverse direction to coil current, and nerve impulses is generated as a result of stimulation of neurons by this eddy current. This type of Transcranial Magnetic Stimulation is being used in clinical laboratory tests and cerebral function research, including measurement of nerve conduction velocity.

In recent years, magnetic stimulation has been gathering attention as a therapeutic application for neuropathic pain, Parkinson's disease, depression, etc. With these types of illness, there are cases where results are not witnessed with treatment using medicines. For example, for intractable neuropathic pain there is a method of treatment where electrical stimulation is given to the brain by implanting electrodes in the brain. However, this method of treatment requires a craniotomy, and so many patients are unwilling to have it performed.

Repetitive transcranial magnetic stimulation, where non-invasive magnetic stimulation, that does not require surgery, is repeatedly carried out, is therefore being researched as a method of treatment. With medical treatment for intractable neuropathic pain, it is being reported that pain relief effects have been attained at about one day after having carried out magnetic stimulation on the cerebral primary motor cortex.

However, a conventional magnetic stimulation device has a weight of about 70 kg, and at the time of installation electrical work is necessary in order to be able to supply electrical power from a 200 V power supply, which means that the device can only be used in well equipped medical facilities. Also, at the time of actual treatment, since it is necessary to determine stimulation position while referencing patient MRI data in accordance with the disorder to be treated, medical treatment by a medical worker who is experienced with that situation is necessary. With the treatment of intractable neuropathic pain, it is necessary to carry out positioning of a coil on the primary motor cortex, which constitutes the target, in units of 1 mm.

With transcranial magnetic stimulation therapy, as a stimulation coil for magnetic stimulation, currently various forms have been proposed, including a circular coil and a FIG. 8 coil (a coil that is wound more or less in the shape of the number "8"), and further a quatrefoil coil, a Hesed coil, and a coil having multiple small circular coils arranged on the surface of a head section, and currently the circular coil and figure 8 coil are mainly being utilized.

A figure 8 coil (refer to patent publication 1 and patent publication 2 below) has two circular coils, formed in series using a single conductor, arranged partially overlapping, and by having electrical current flow in opposite directions in these circular coils it is possible to cause eddy currents to converge directly beneath a section where the coils cross, and stimulate a local region.

On the other hand, depending on the object of treatment or on the personal symptoms of the patient, there may be cases where instead of localized stimulation, stimulation over a wider range is effective.

Also, with a coil that focuses stimulation locally there is a need to accurately determine position on the target region, and in this case it is necessary to implement accurate positioning using a navigation system or the like.

As well as carrying out development of magnetic stimulation used in home treatment, there has also been advancement in development of navigation systems for determining stimulation position by a non-medical worker. According to the system, first a patient is fitted at the hospital with glasses having a magnetic sensor, and calibration is carried out using a permanent magnet in order to attach the glasses at the same position every time. Next, a doctor specifies optimum stimulation position using a procedure that combines a patient MRI image and an optical tracking coordinate system, and the optimum stimulation position, and data for random positions in a range of 5 cm around the optimum stimulation position, are stored. By storing surrounding position data, it is possible to for the patient to visually know where a coil currently is when determining coil position.

At the time of home treatment, first calibration of the glasses is carried out. After that, three-dimensional position is measured by comparing position of permanent magnets that are fitted to the stimulation coil with data. By visually confirming current position of the coil and optimum stimulation position, it is possible to instinctively carry out positioning of the coil.

By experimentation it is found that navigation error of this navigation system is a maximum of, for example, 5 mm from the optimum stimulation position, while on the other hand if the figure 8 coil that was described previously has an irradiation position (optimum stimulation position) within this 5 mm, it is possible to provide therapeutically effective stimulation of the target region. This means that at a stimulation position that has been guided by using a navigation system, if a treatment device that carries out magnetic stimulation with a figure-8 coil is used, there is a possibility that a region that is to be radiated (optimum stimulation position) will not be within the effective stimulation range of the treatment coil, and so it will be difficult to accurately carry out stimulation to the treatment region. Accordingly, it is necessary to develop a coil that is capable of generating eddy current uniformly over a wider range, such that in a case where there is a region to be radiated within, for example, 10 mm, a target region can be stimulated in a therapeutically effective manner.

Therefore, in order to implement a stimulation coil having high robustness (specifically, being capable of generating uniform eddy current over a wider range), a dome type coil device (in the specification below, referred to as "dome type coil") has been proposed by the present inventors (refer to patent publication 3 below). This dome type coil can cause eddy current to be generated over a wide range compared to the figure 8 coil, and there is also the desirable property of being able to reduce inductance while maintaining inducement of eddy current over a wide range.

However, while the dome type coil shown in patent publication 3 below can generate an induced electrical field over a wide range compared to the figure-8 coil, as already stated, there is a problem in that electrical field intensity is low in a case where the same electrical current as with the figure-8 coil has been applied (approximately ¼ under the same current application conditions).

In a case where induced electrical field is small, more electrical current must be applied in order to compensate for this, which means that not only is there a possibility of device cost and installation cost being increased due to boost circuits and capacitors being increased in size, there was also a problem in that that coil itself heats up rapidly and it is necessary to take measures to deal with this.

Accordingly, the present inventors have carried out various experiments regarding coil shape and design parameters, and as a result have acquired knowledge regarding shapes that have the advantage of being able to provide the same wide induced electrical field as a dome type coil while being able to generate a stronger induced electrical field with approximately the same applied current, and that can comprises a coil that does not obtain a value of inductance that has deviated.

PRIOR ART PUBLICATIONS

Patent Publications

Patent Publication 1: Japanese patent laid-open No. 2012-125546
Patent publication 2: International Patent publication No. 2010/147064
Patent publication 3: International Patent publication No. 2015/122506 (for example, FIG. 6)

SUMMARY OF THE INVENTION

Technical Problem

The present invention has been conceived based on the previously described knowledge. The main object of the present invention is to provide a coil that can give the same wide induced electrical field as a dome type coil, and that can generate a strong induced electrical field with the same applied current as for a dome type coil, and that can further keep inductance to a small value.

Solution to the Problem

Means for solving the above described problem can be described as in the following aspects.

(Aspect 1)
A coil, arranged close to a surface of an object, for causing an induced electrical field to be generated inside the object, wherein
the coil has 1st to Nth turns,
the 1st to the Nth turns are respectively provided with an actuation part for flow of electrical current in one direction and a connection part for flow of electrical current in a direction opposite to the one direction,
the actuation parts of the 1st to Nth turns are arranged parallel to each other, and along a surface of the object or along a surface that is close to the surface of the object,
the connection parts are arranged within a space in which the connection parts do not face the surface of the object over the actuation parts of the 1st to Nth turns, and the connection parts are positioned at the sides with respect to the extending direction of the actuation parts, and
N is an integer of 2 or greater.

(Aspect 2)
The coil of aspect 1, wherein the connection parts of 1st to Pth turns, within the 1st to Nth turns, are arranged over the actuation parts at positions on the opposite side to the connection parts of P+1th to Nth turns.

(Aspect 3)
The coil of aspect 1 or aspect 3, wherein the connection parts are formed in a substantially arcuate shape.

(Aspect 4)
The coil of any one of aspect 1 to aspect 3, wherein the surface on which the actuation parts are arranged is formed having a substantially arcuate cross section.

(Aspect 5)
The coil of any one of aspect 1 to aspect 4, wherein the actuation parts of the 1st to Nth turns are arranged at equal intervals.

(Aspect 6)
The coil of any one of aspect 1 to aspect 5, wherein the object is a living body.

(Aspect 7)
The coil of any one of aspect 1 to aspect 5, wherein the object is the head of an animal, and
the coil is configured to produce induced current within the brain of the head as a result of the induced electrical field.

(Aspect 8)
The coil of any one of aspect 1 to aspect 7, further provided with a core member, and wherein
the core member is configured to reduce magnetic resistance of a magnetic circuit that is generated by the 1st to Nth turns, and
the core member is arranged at opposite side to the object, over the actuation parts.

(Aspect 9)
The coil of aspect 8, wherein the core member has a plurality of regions of differing relative permeability.

(Aspect 10)
The coil of aspect 8 or aspect 9, wherein the core member is provided with first parts that are arranged at positions that face the actuation parts, and second parts that are arranged at positions facing the connection parts,
the first parts are provided with a plurality of elongated first core bodies that extend in a direction that is not parallel to the extension direction of the actuation parts, and
the second parts are provided with a plurality of elongated second core bodies that extend in a direction that is substantially parallel to the extension direction of the actuation parts.

(Aspect 11)
A magnetic stimulation device comprising the coil of any one of aspect 1 to aspect 10, and a power supply section for supplying a given electrical current to the coil.

(Aspect 12)
A coil, arranged close to a surface of an object, for causing an induced electrical field to be generated inside the object, wherein
a series of conductors of the coil, running from an input terminal to an output terminal, are made up of
(1) a plurality of actuation conductors used in the induced electrical field generations, and
(2) connection conductors that connect the plurality of actuation conductors together, and that are configured in a form whereby effect on intensity of an induced electrical field that has been generated by the actuation conductors can be substantially ignored.

(Aspect 13)

A magnetic stimulation device comprising a coil, arranged close to a surface of an object, for causing an induced electrical field to be generated inside the object, and a support, wherein the coil has 1st to Nth turns, the 1st to Nth turns are respectively provided with an actuation part for flow of electrical current in one direction and a connection part for flow of electrical current in a direction opposite to the one direction, the actuation parts of the 1st to Nth turns are arranged substantially parallel to each other, the connection parts are arranged within spaces, laterally with respect to the extension direction of the actuation parts, the actuation parts are supported by the support, a lower surface of the support is formed in a substantially flat shape, and N is an integer of 2 or greater.

(Aspect 14)

A magnetic stimulation device of aspect 13, wherein the surface of the object is a substantially spherical shape, and a lower surface of the support is therefore configured to contact a surface of the object substantially at the center of the support.

Advantageous Effect

According to the present invention it is possible to provide a coil with which efficiency of generating an induced electrical field with respect to applied current is high even if design of area of an actuation part is widened so as to obtain a comparatively wide induced electrical field, and that can also keep inductance to a low value.

Also, according to the present invention, since change rate of magnetic flux density at a stimulation point with respect to change in distance from a coil surface to the stimulation point is configured to be less than a given value, it is possible to reduce unpleasantness that is attributable to stimulating close to the scalp as well, at the time of treatment where an irradiation target within the brain is subjected to magnetic stimulation.

BRIEF DESCRIPTION OF THE DRAWINGS

FIG. 40 is a graph for comparing a coil of practical example 3 (flat-d), a coil of practical example 1 (Double-D) and a conventional figure 8 coil (FIG. 8), with the horizontal axis being measurement position (distance from the coil in the object direction (lower surface direction)) and the vertical axis being magnetic flux density.

DESCRIPTION OF THE EMBODIMENTS

A magnetic stimulation device of one embodiment of the present invention will be described in the following with reference to the attached drawings. The magnetic stimulation device of this embodiment is a device for carrying out transcranial magnetic stimulation, which is a method of imparting stimulation to the brain using induced current generated using a variable magnetic field.

(Structure of the Magnetic Stimulation Device)

Figure 4:
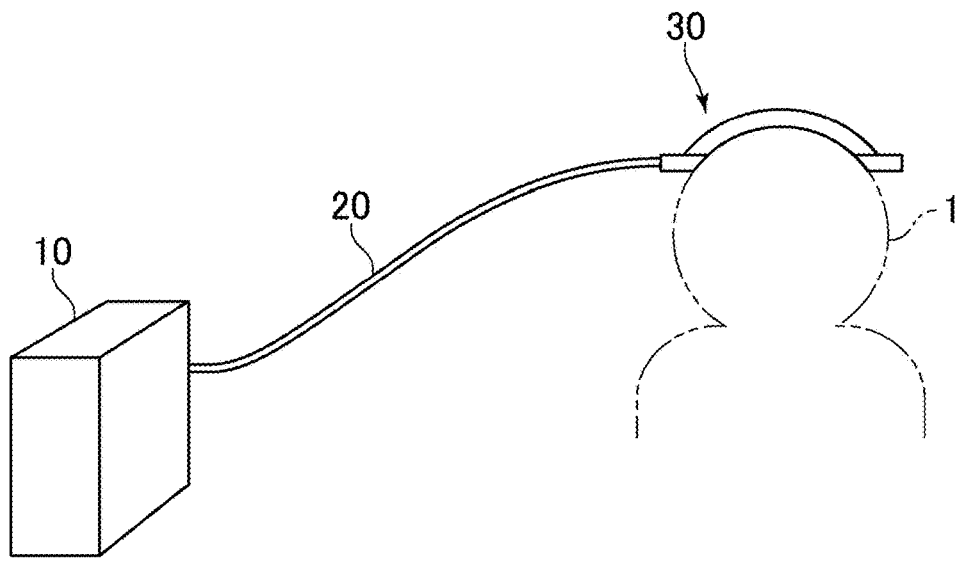
FIG. 4 is a schematic explanatory drawing for describing the structure of a magnetic stimulation device of one embodiment of the present invention.

The magnetic stimulation device of this embodiment (refer to FIG. 4) comprises a power supply section 10, cable 20 and application part 30. This magnetic stimulation device generates an induced current within an object 1. Here, with this embodiment, a living body, in particular the head of a person, is used as the object 1. In the following, therefore, head 1 may be used instead of object 1.

(Power Supply Section)

The power supply section 10 is configured to cause a given induced current to be generated within the object 1, by supplying a given current to a coil 31 (described later) of the application part 30. Current supplied from the power supply section 10 may have a direct current component provided it has an alternating current component that can generate induced current. Accordingly, as electrical current it is possible to use various waveforms according to use, such as a monophasic pulse form or a biphasic pulse form. A pulse generation period is set appropriately in accordance with usage. Since it is possible to use a similar power supply as in the related art (refer, for example, to previously described patent publication 3) as this type of power supply section 10, more detailed description has been omitted.

(Cable)

The cable 20 is configured to supply a given current from the power supply section 10 to the coil 31 (described later) of the application part 30. The cable 20 has a certain degree of flexibility, so that the application part 30 can be arranged at a suitable position on the head 1 of a subject. It is also possible to use a similar cable to that in the related art for the cable 20, and so more detailed description has been omitted.

(Application Part)

The application part 30 (refer to FIG. 5) is provided with the previously described coil 31 and a support 32 that supports this coil 31.

(Coil)

The coil 31 (refer to FIG. 6 to FIG. 8) is arranged close to the surface of the object (namely the head of the subject) 1, and is configured to generate an induced electrical field within the object 1.

The coil 31 of this embodiment has 1st to Nth turns 311 to 31N. Here N is an integer of 2 or more, preferably 3 or more, the induced electrical field becomes stronger with the number of turns, and it becomes easy to widen a target region. On the other hand, if appropriate inductance is taken into consideration, the number of turns is appropriately 20 or less, more preferably 14 or less. With the illustrated example, the number of turns N=14.

Figure 7:
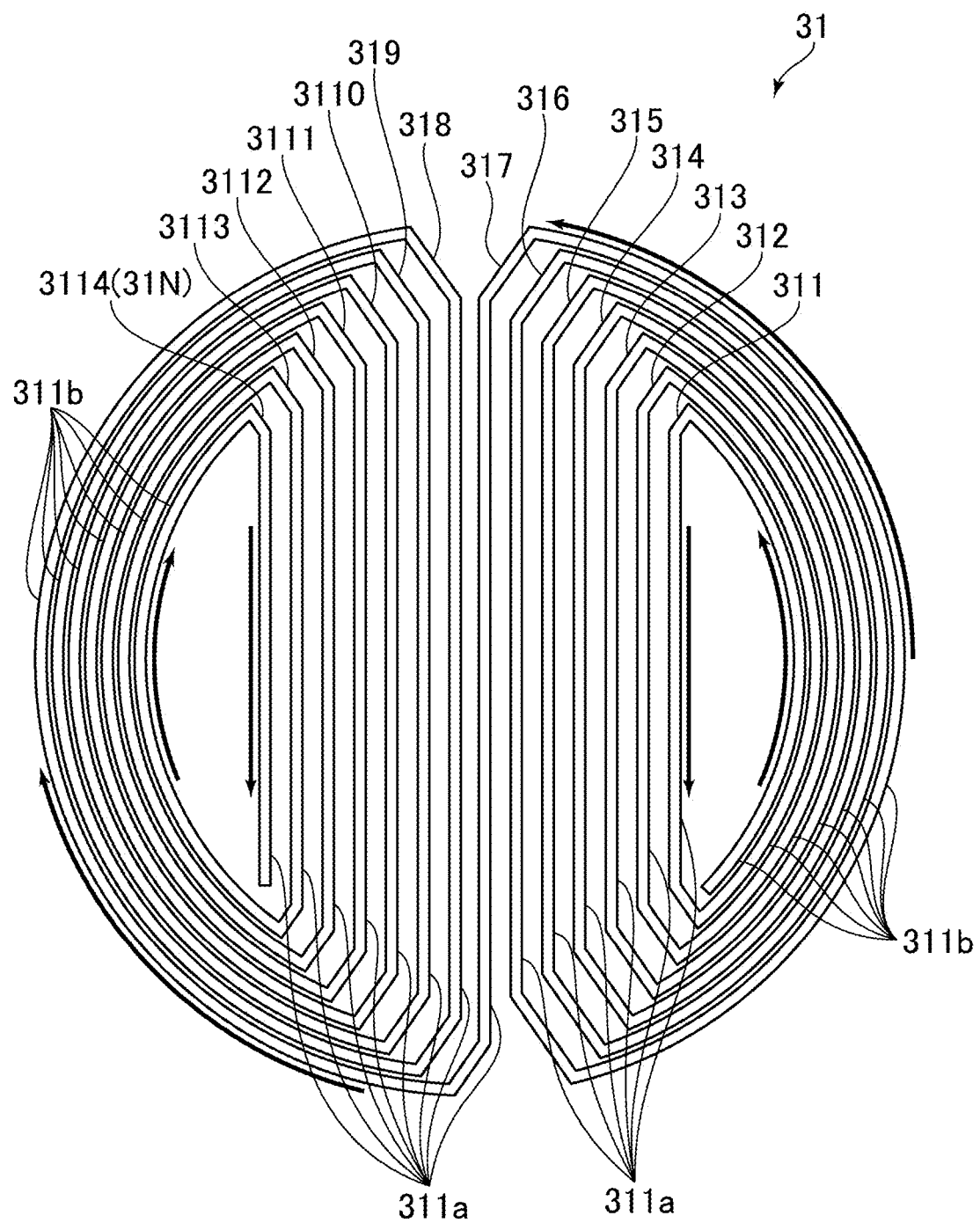
FIG. 7 is a plan view for describing an arrangement state of a coil used in the application part of FIG. 6.
Figure 8:
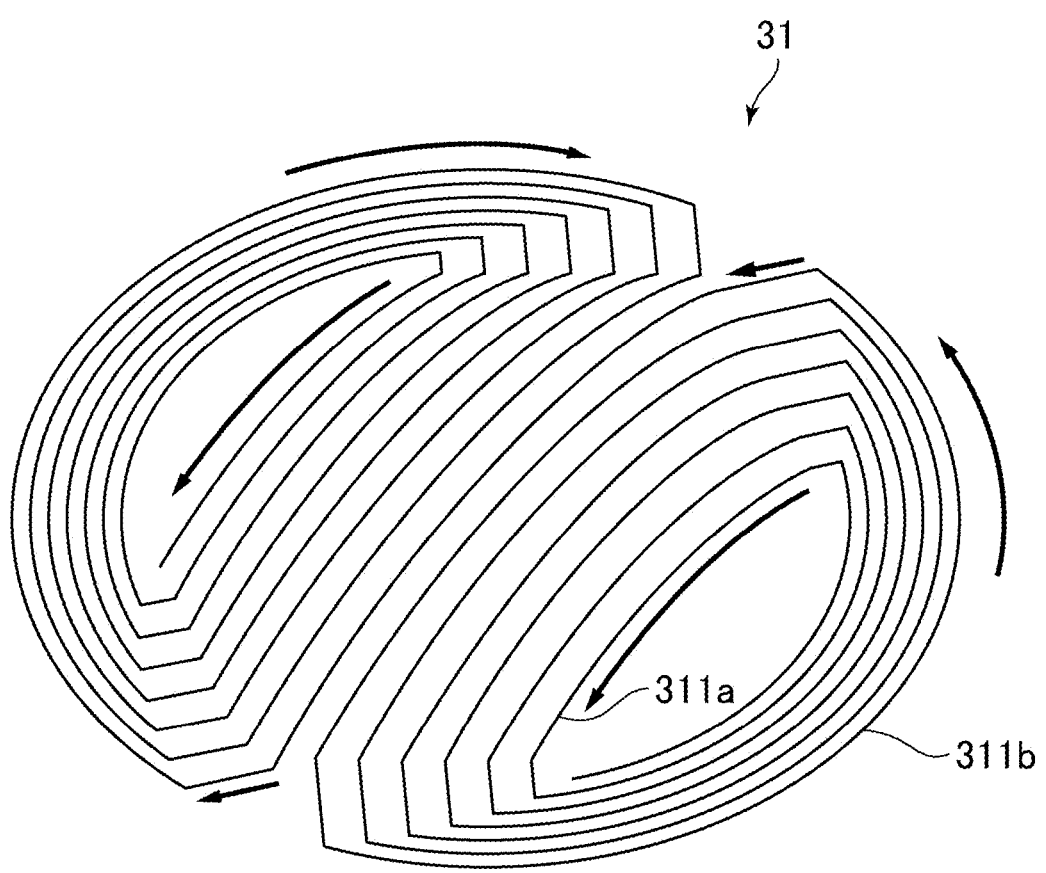
FIG. 8 is an explanatory drawing for describing flow direction of electrical current in the coil.

The 1st to Nth turns 311 to 31N of the coil 31 are respectively provided with actuation parts 311a for current in one direction to flow, and connection parts 311b for current in the opposite direction to the one direction to flow. Here, the actuation parts are provided for each turn, but with this specification the same reference numeral 311a is assigned for each actuation part. The same applies for the connection parts 311b. Also, "current in the opposite direction" described previously is not a direction along a conducting wire direction, but means opposite to an orientation within spaces in which the coil is arranged. Specifically, it does not mean electrical current −i in a direction that is opposite to current i that flows in the coil. In FIG. 7 and FIG. 8 flow directions of electrical current in the coil are shown by arrows.

Figure 5:
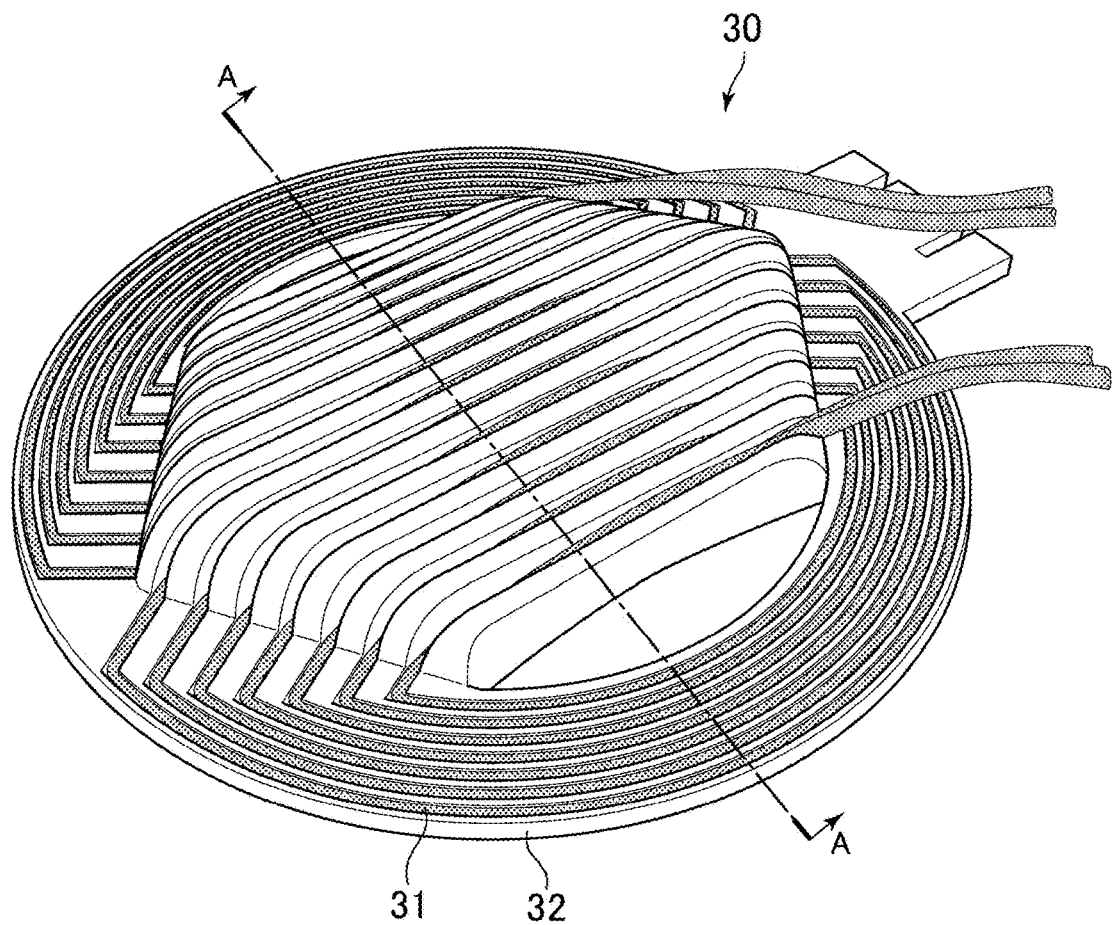
FIG. 5 is a perspective drawing, with an application part used in the device of FIG. 4 enlarged.
Figure 6:
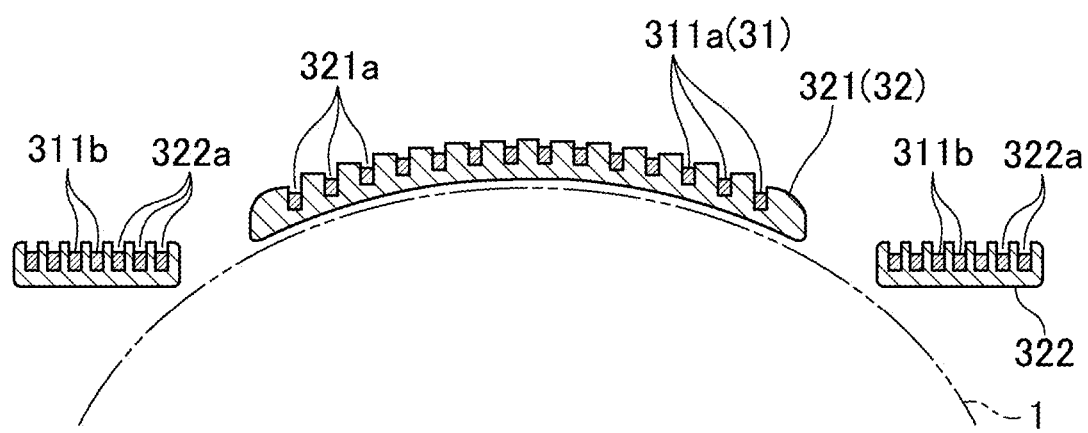
FIG. 6 is a cross-sectional drawing along line A-A in FIG. 5, and shows the application part in a state of being placed on an upper surface of an object (head).

By supporting the coil 31 of this embodiment with the support 32, spatial arrangement state of the coil is regulated (refer to FIG. 5 and FIG. 6). Specifically, the plurality of actuation parts 311a of the 1st to Nth turns 311 to 31N are arranged substantially parallel to each other, and are arranged along a surface of the object 1 or a surface that approximates to the surface of the object 1. More specifically, since the head of a person can be approximated to substantially a spherical surface, the actuation parts 311a are arranged so as to run along a spherical surface (in more detail, part of a spherical surface). With this embodiment, a surface on which the actuation parts 311a are arranged (specifically, an upper surface of a contact section 321 of the support 32, which will be described later) is made a substantially spherical surface.

Further, with this embodiment, actuation parts 311a of the 1st to Nth turns are arranged at equal intervals.

Also, a plurality of connection parts 311b of the 1st to Nth turns 311 to 31N are arranged within the space in which the connection parts do not face the surface of the object 1 over the actuation parts 311a of the 1st to Nth turns, and the connection parts 311b are positioned at the sides with respect to the extension direction of the actuation parts 311a (refer to FIG. 6). More specifically, the connection parts 311b are arranged periodically in a direction that is substantially orthogonal to the extension direction of the actuation parts 311a (vertical direction in the drawing of FIG. 7)

Also, with this embodiment, the connection parts 311b of 1st to Pth turns, among the 1st to Nth turns, are arranged at an opposite side to connection parts 311b of P+1th to Nth turns, over the actuation parts 311a (refer to FIG. 7). With the example of FIG. 6 N=14 and P=7, but these numbers are not limiting, and can be changed in accordance with various setting conditions.

The connection parts 311b formed so as to be substantially arcuate in planar view (refer to FIG. 7). Also, connection parts 311b arranged in a divided manner to the left and right of the actuation parts 311a are left right symmetrical either side of the actuation parts 311a. Further, connection parts 311b of one side of the actuation parts 311a are substantially concentric. It should be noted that the number of connection parts 311b on the left and right sides may be different. Specifically, the shape of the coil 31 need not be left right symmetrical, and maybe asymmetrical. For example, a structure where the number of turns N=14, and P=8, is also possible. Obviously these numerical values are merely one example, and these numerical values are not restricted.

In other words, the coil of this practical example is a coil that is arranged close to a surface of an object for generating an induced electrical field within the object, and a series of conducting wires possessed by the coil, that run from an input end to an output end, comprise:
(1) a plurality of actuation conductors used in induced electrical field generation, and
(2) connection conductors that connect the plurality of actuation conductors together, and that are configured in a form whereby effect on intensity of an induced electrical field that has generated by the actuation conductors can be substantially ignored.
(Support)

The support 32 is provided with a contact section 321 that is capable of contacting a surface of the object 1, and a flange section 322 that is formed on an outer peripheral edge of the contact section 321.

The contact section 321 is formed either in a substantially plate shape that has been curved so as to form part of a spherical surface (namely in a spherical surface shape), or substantially disk-shaped, and as a result it is possible for part of a head 1, as an object, to be accommodated by a lower surface of the contact section 321 (refer to FIG. 6).

Figure 9:
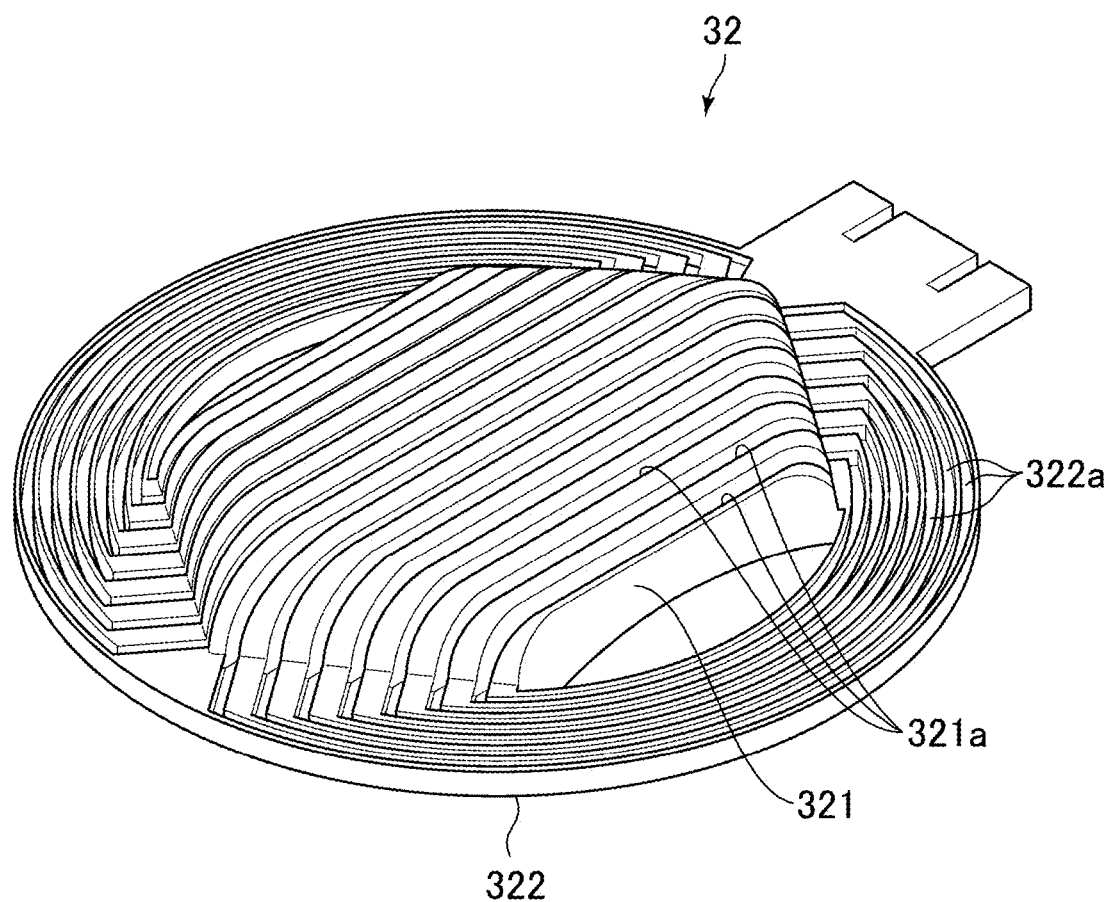
FIG. 9 is a perspective drawing of a support used in the application part of FIG. 6.
Figure 10:
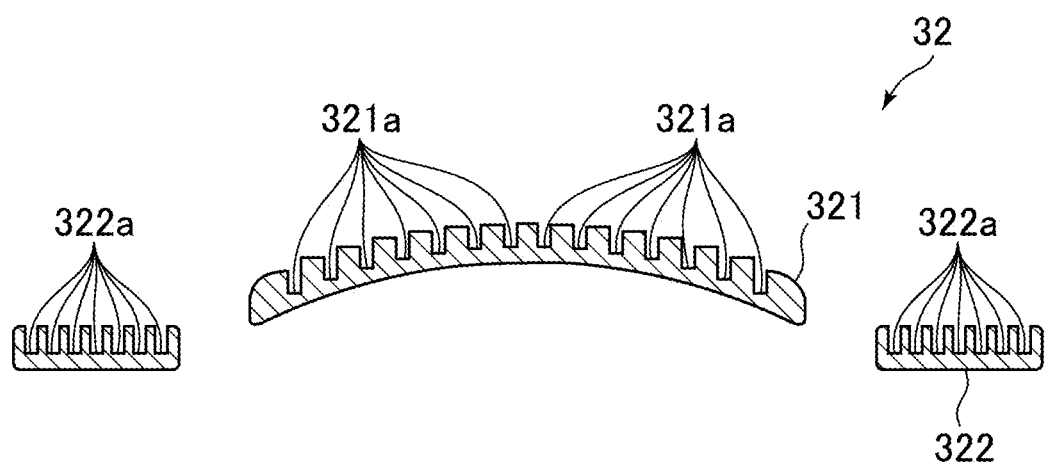
FIG. 10 is a cross sectional view of the support, for a position corresponding to FIG. 6.

Grooves 321a for accommodating the actuation parts 311a of the coil 31 and carrying out alignment of these actuation parts 311a are formed on the upper surface of the contact section 321 (refer to FIG. 6 and FIG. 10). With this embodiment, the grooves 321a are formed along an upper surface of the contact section 321, substantially parallel to each other and at equal intervals, similarly to the actuation parts 311a (refer to FIG. 9).

The flange section 322 is formed extending in an outward direction, from the outer peripheral edge of the contact section 321 (refer to FIG. 9). The flange section 322 of this embodiment is formed in a shape overall that has a substantially flat plate-shape in cross section, and as a result of this it becomes possible to slightly separate the flange section 322 from the substantially spherical surface-shaped object (refer to FIG. 6). Grooves 322a for accommodating the connection parts 311b of the coil 31 and carrying out alignment of these connection parts 311b are formed on the upper surface of the flange section 322 (refer to FIG. 6 and FIG. 10). With this embodiment, the grooves 322a are formed extending along an upper surface of the flange section 322 so as to form concentric circles (or so as to form parallel curves), similarly to with the connection parts 311b (refer to FIG. 9).

Practical Example 1—Design Condition Optimization

Next, design conditions for a coil 31 that is used in this embodiment described previously will be considered, using simulation.

Figure 11:
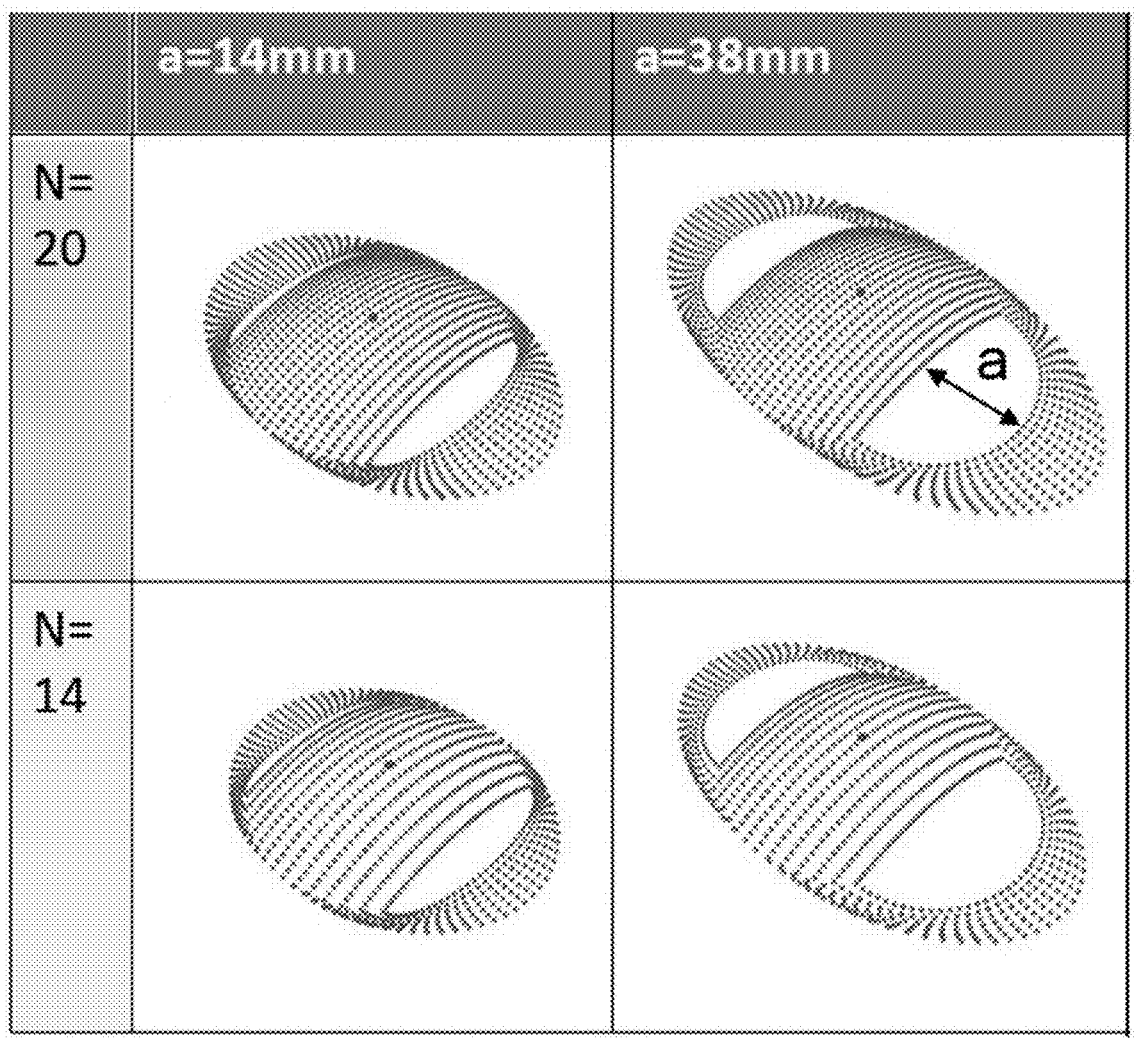
FIG. 11 is an explanatory drawing for describing conditions for simulation using a coil of this embodiment.

In the evaluation below, as well as assuming that that area of the coil 31 of this embodiment (in the following specification it will be referred to as a "double-D coil") that contacts a head 1 (specifically, area that contacts the head by means of the contact section 321 of the support 32) is fixed, minimum interval a (refer to FIG. 11) between the actuation parts 311a and the connection parts 311b, and number of turns N of the coil, will be varied, and what effect these design parameters have on the induced electrical field generated by the coil will be made clear. In addition, once design parameters of a Double-D coil of particularly high practicability (having an inductance that is capable of connection to current drive circuitry, and achieving induced electrical field generation efficiency that is comparable to that of a conventional figure-8 coil) have been determined, comparison with an already known coil will be carried out and effectiveness of the designed coil confirmed.
(Simulation Conditions)

Shape optimization of a Double-D coil is carried out. It should be noted that numerical values for design shown in the following are merely one example, and the scope of the present invention is not to be limited by these values.

First, a radius of curvature of a surface (spherical surface) on which the actuation parts 311a are arranged is made 100 mm, overall width (width in the arrangement direction) of the actuation parts 311a is made 78 mm, and radius of a cover range by bottom surfaces of all the actuation parts 311a (namely half of the maximum length of the actuation parts 311a) is made 56 mm. The previously described minimum interval a is made variable, and this was varied from 14 mm to 38 mm (refer to FIG. 11). Also, overall number of windings N of the coil 31 is varied from 14 to 20 with cover area of the head by the conducting wires of the coil 31 fixed (refer to FIG. 11). It should be noted that in FIG. 11 the coil has been described in a simplified manner ignoring the spiral winding structure. The cross sectional shape of the coil conducting wires is assumed to have a width of 2 mm and a height of 6 mm.

Figure 1:
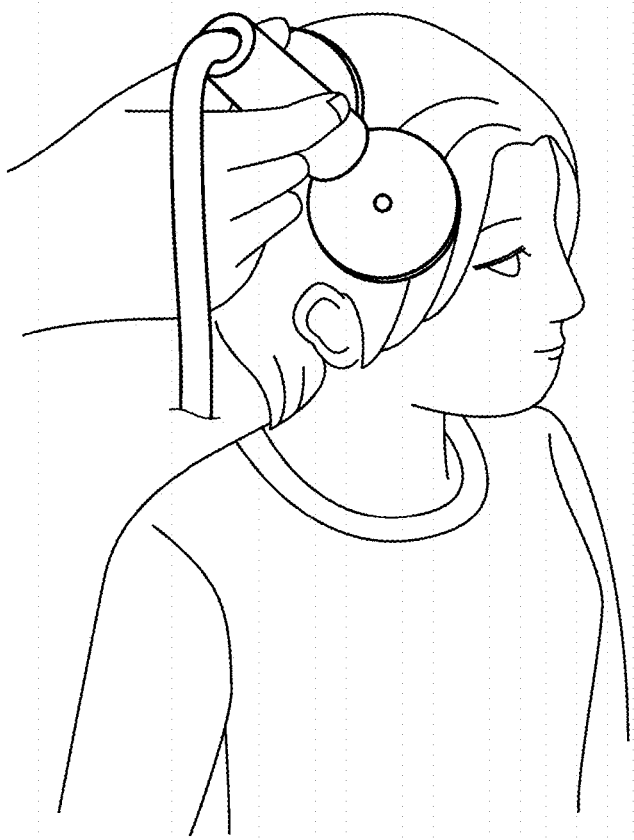
FIG. 1 is an explanatory drawing for describing a usage method of a conventional magnetic stimulation device.
Figure 2:
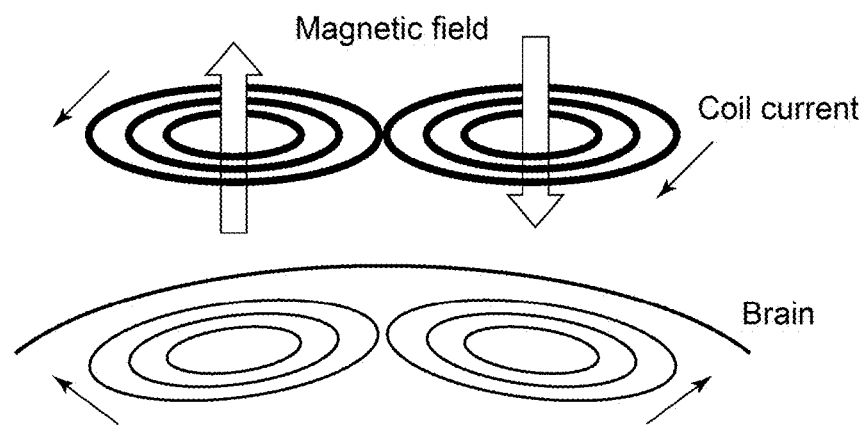
FIG. 2 is an explanatory drawing showing a relationship between a magnetic field generated by a coil used in a conventional magnetic stimulation device and induced current occurring at the surface of the brain.
Figure 3:
FIG. 3 is an explanatory drawing for describing a usage method of a conventional magnetic stimulation device.

In the simulation, a coil 31 was positioned 1 cm directly above a conducting hemisphere of 75 mm radius, and induced electrical field when pulse current of a maximum current of 5.3 kA and a pulse frequency of 3.4 kHz was applied was obtained by calculation. Electrical field intensity was evaluated using average values within a sphere of 10 mm radius from a stimulation center (center portion of the surface of an object that is made the target, for example, specific position within the motor area of the brain). With maximum intensity of induced electrical field generated by applied current as a reference, spread of the electric field was evaluated using total area of voxels in which an electric field of 50% or more of this maximum intensity was generated. In the calculation, a Scalar Potential Finite-Difference method (SPFD method) was utilized, using the present inventor's original software (an outline of that software will be described later). Besides calculation using a finite difference, coil inductance was subjected to approximation calculation using Neumann's formula. In Neumann's formula, inductance L of a fine track group C is obtained using equations (1), (2) and (3). It should be noted that in FIG. 3, the cross sectional shape of the conductor bodies is made a rectangle of width w and height h, and wiring portion lengths of the conductor bodies are made l. $m_{i,j}$ represents partial inductances of each fine track, and $s_i$, $s_j$ represents respective fine track current vectors. Distance r between associated fine tracks, which are torsional positions, is simply approximated as distance between center points of each fine wire portion with this example.

$$L = \sum_{i=1}^{P} \sum_{j=1}^{P} m_{ij} \quad (1)$$

$$m_{ij} = \frac{\mu_0}{4\pi} \int_{C_i} \int_{C_j} \frac{ds_i \cdot ds_j}{r} \quad (2)$$

$$m_{ii} = \frac{\mu_0 l}{2\pi} \left( \ln \frac{2l}{w+h} + 0.50049 + \frac{w+h}{3l} \right) \quad (3)$$

Also, in addition to simulation using an SPFD method, in order to be doubly sure, simulation using a finite element method is simultaneously carried out, and a more accurate inductance obtained from a magnetic field generated in an air region, and strength of magnetic flux density, are obtained. For the purpose of comparison with an existing coil, three models were prepared for a figure 8 coil (previously described patent publications 1 and 2) having a total of 20 turns, an external radius (radius at the coil circumference) of 100 mm and a conductor gap of 1 mm, a circular coil having a total of 10 turns and an external radius of 100 mm, and a dome type coil having a height of 39 mm, and external radius of 66 mm, and a width of 78 mm, and inductance, strength of magnetic flux density, and electrical field intensity of a hemisphere model surface layer part (depth of 1 mm from the surface) were obtained. It should be noted that Photo-Series (Photon Co. Ltd.) was used in the finite element method simulation.

(Result 1/Examination: Change in Induced Electrical Field Due to Coil Internal Diameter Width)

Figure 12:
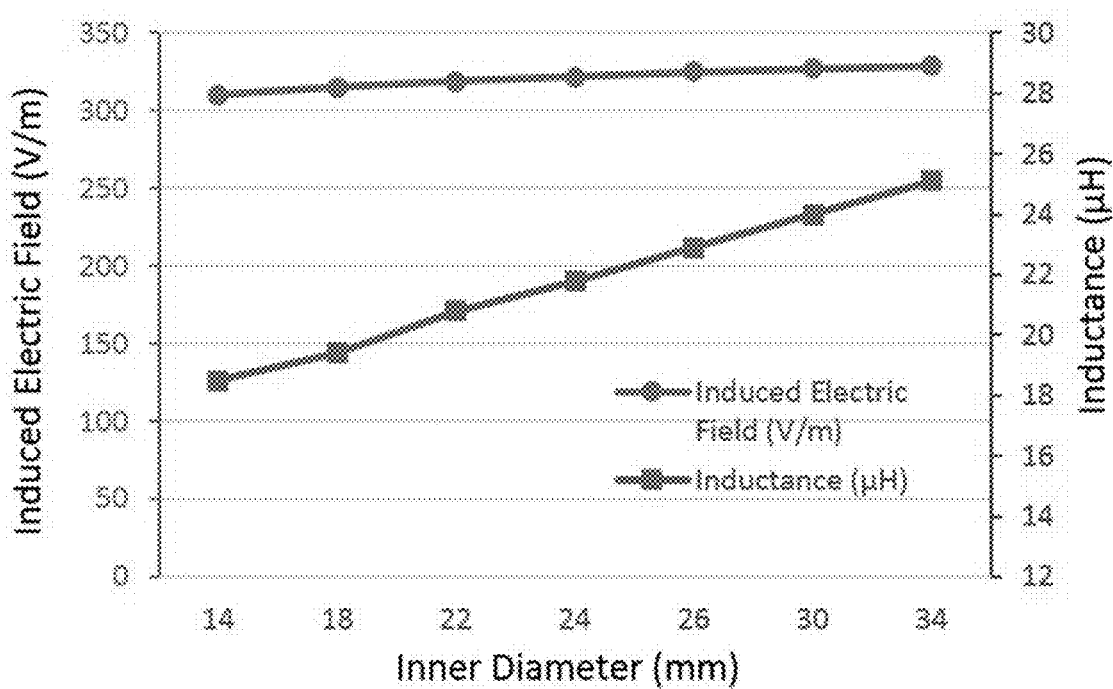
FIG. 12 is a graph showing results of simulation, with the horizontal axis showing inner diameter a, and the vertical axis showing induced electrical field intensity and inductance.

Results are collected together in table 1 for variation in electrical field intensity, inductance, and spread of induced electrical field for a case where a coil of 20 turns was used and the inner diameter width (minimum interval) a of that coil was varied. FIG. 12 shows electrical field intensity and inductance in a graph.

TABLE 1

| Variation in coil characteristic with change in inner diameter width | | | | | | | |
|---|---|---|---|---|---|---|---|
| (inner diameter width mm, number of turns 20) | 14 mm | 18 mm | 22 mm | 26 mm | 30 mm | 34 mm | 38 mm |
| Electric field intensity (V/m) | 310 | 315 | 319 | 322 | 325 | 327 | 329 |
| Inductance (µH) | 18.5 | 19.4 | 20.8 | 21.8 | 22.9 | 24.0 | 25.1 |
| Induced electrical field spread (cm2) | 34.4 | 35.6 | 36.8 | 37.8 | 38.6 | 39.3 | 40.0 |

According to the obtained results, it is found that while the wider the width a of the coil sides becomes, the greater inductance rises, there is not much variation in intensity and spread of the induced electrical field that can be generated in a head model (object). If there is almost no variation in the induced electrical field, lower inductance is preferable, and so it can be concluded that inner diameter width a of the Double-D coil should be made as narrow as possible to a limit where the surface of the head and the coil (specifically, the lower surface of the support of the coil) interfere with one another. Also, a value such as inductance=18.5 µH in the case where number of turns N=20 and width a=14 mm is a large value for connecting to a commercially available drive circuit, and it is preferable to further lower inductance from this value by reducing the number of turns.

(Result 2/Examination: Change in Induced Electrical Field Due to Number of Turns of Head Contacting Surface)

Figure 13:
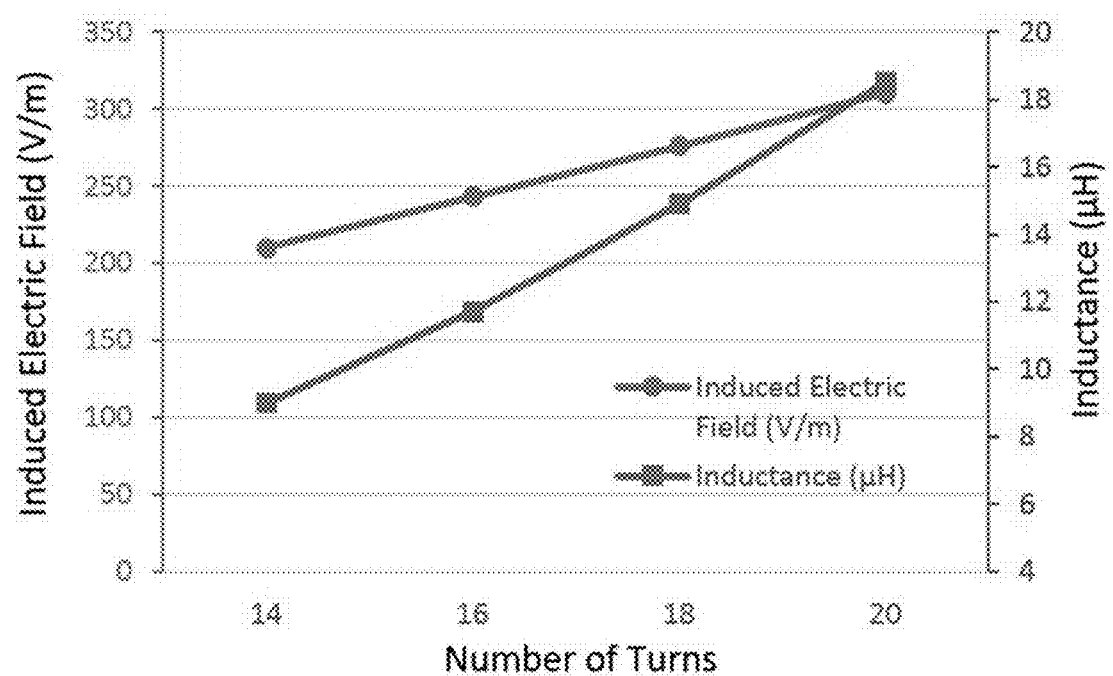
FIG. 13 is a graph showing results of simulation, with the horizontal axis showing number of turns N and the vertical axis showing induced electrical field intensity and inductance.

Results for variation in electrical field intensity, inductance and induced electrical field spread for a number of coil turns N (variable) with inner diameter width a=14 mm are collected together in table 2. FIG. 13 shows electrical field intensity and inductance in a graph.

TABLE 2

| Change In Coil Characteristics With Change In Number Of Turns | | | | |
|---|---|---|---|---|
| (Inner Diameter 14 mm, Number Of Turns) | N14 | N16 | N18 | N20 |
| Electrical Field Intensity (V/m) | 210 | 243 | 276 | 310 |
| Inductance (µH) | 9.0 | 11.7 | 14.9 | 18.5 |
| Induced Electrical Field Spread (cm$^2$) | 33.4 | 33.8 | 34.1 | 34.4 |

From the obtained results it will be understood that there is almost no variation in induced electrical field spread in accordance with number of turns. It will also be understood that while it is possible to lower inductance by lowering the number of turns of the coil, intensity of the induced electrical field will also be lowered significantly. It is desirable to have an inductance of about 10 µH or lower for connection to a commercially available drive circuit, and taking this into account 14 is appropriate for the total number of turns of a coil.

Here, with an actual coil it has been considered to widen conductor interval in order to simplify production. If this is done then interlinkage flux of the coil is increased, and it is possible to increase the inductance. Overall inductance is also increased by the cable 20 that connects the drive circuit and the coil. Accordingly, as a design value with the coil 31 it can be considered beneficial to allow a further margin compared to 10 μH. With this example, descriptions regarding comparison with an existing coil and specific manufacture will be given by adopting a width a=14 mm and number of turns N=14, leaving a margin for the inductance value.
(Result 3/Evaluation-Comparison with Existing Coil)

Figure 14:
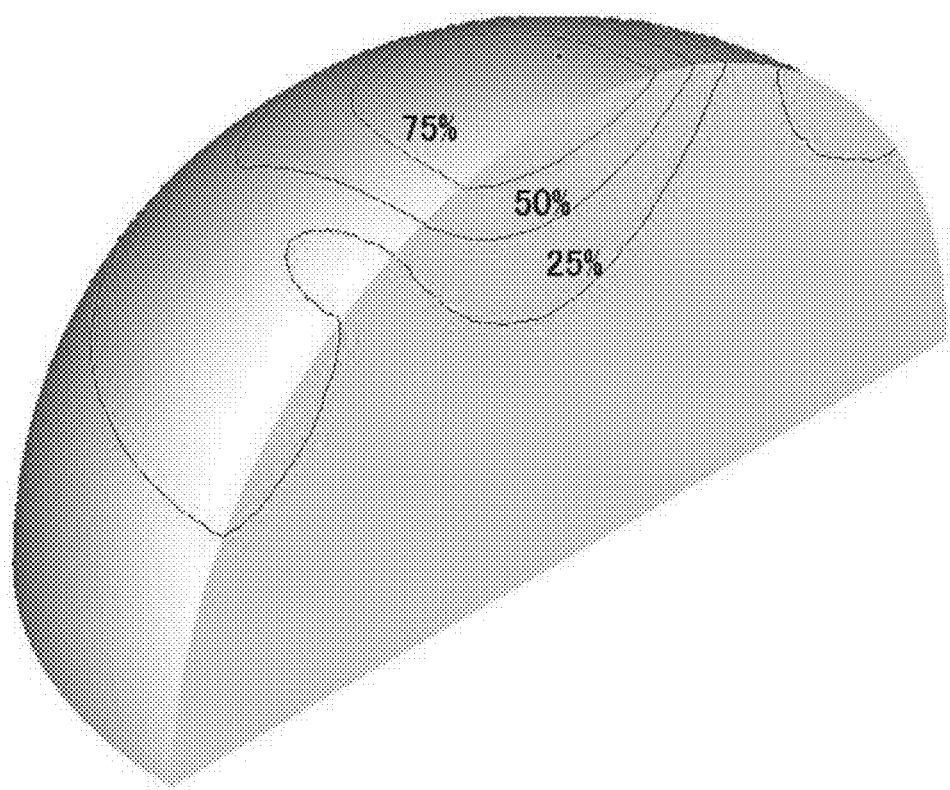
FIG. 14 is an explanatory drawing of the results from simulation, and is an explanatory drawing for describing spread of an electric field generated by the coil of this embodiment.
Figure 15:
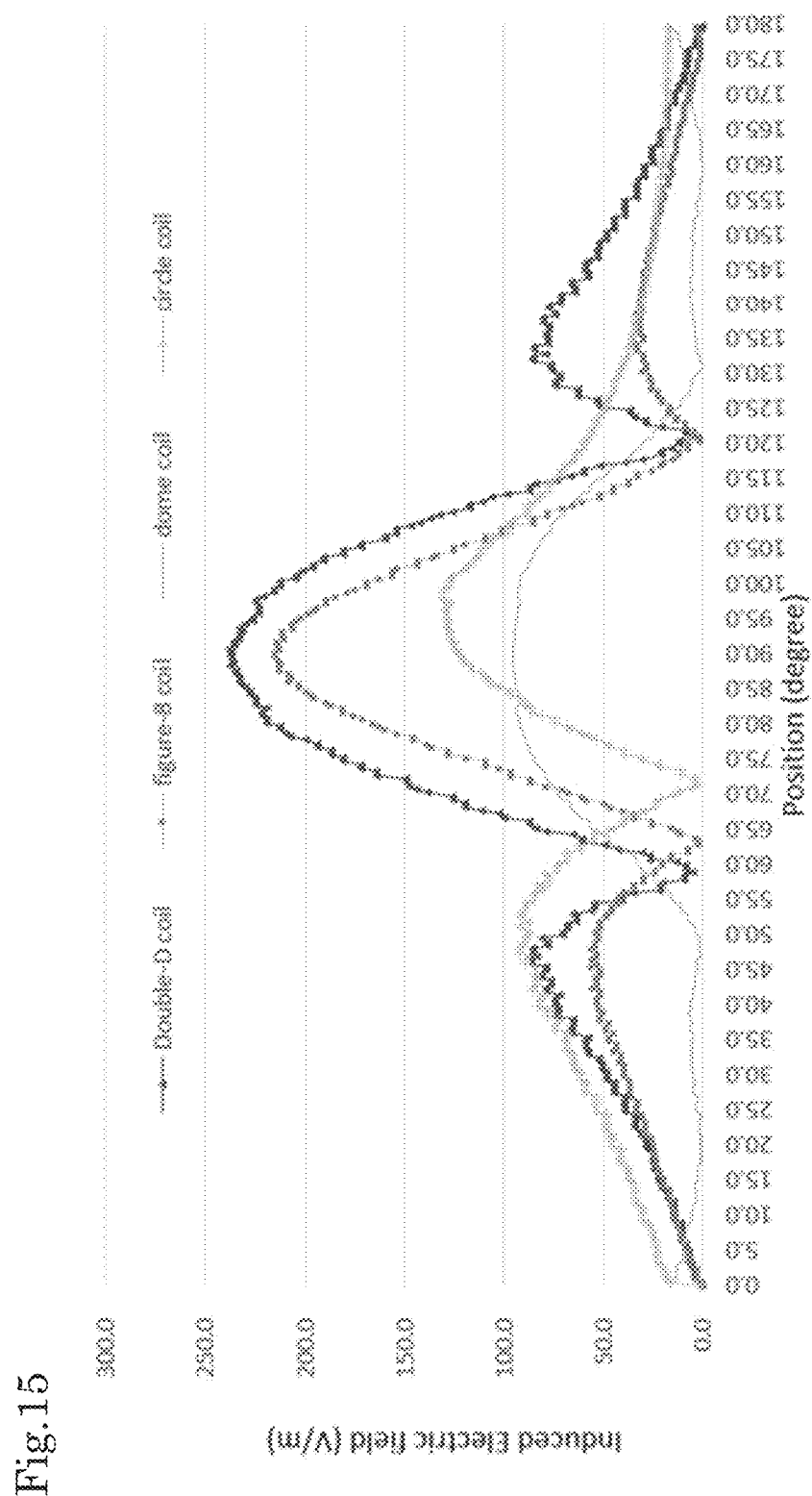
FIG. 15 is a graph in which various conventional coils are compared with the coil of this embodiment, with the horizontal axis being measurement position (rotational angle about the coil center) and the vertical axis being induced electrical field intensity.
Figure 16:
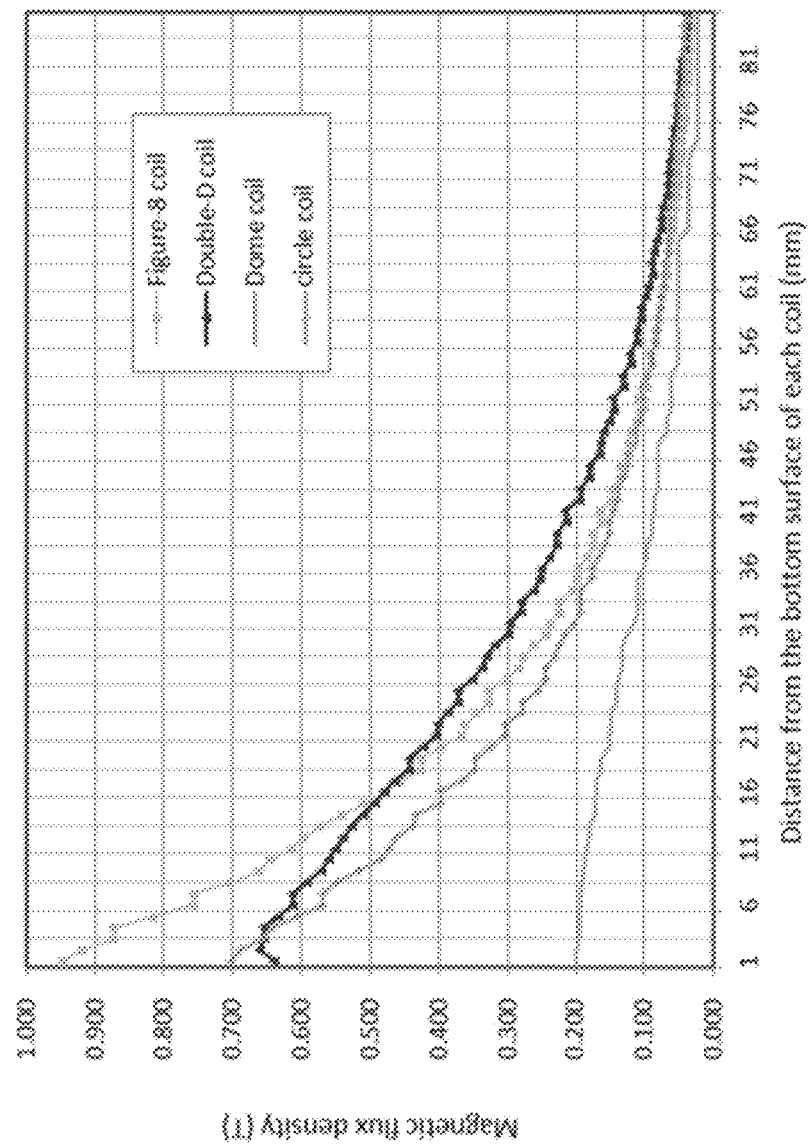
FIG. 16 is a graph that compares various conventional coils with the coil of this embodiment, with the horizontal axis being measurement position (distance from coil in the object direction (lower surface direction)) and the vertical axis being magnetic flux density.

As a simulation result using the finite element method, spread of an electric field with a hemisphere model (model where an object is made a hemisphere shape), in a case where a FIG. 8 coil and a Double-D coil are used, is shown in FIG. 14. With this drawing, normalized electrical field intensity is shown with a maximum value as 100%. Also, comparison with each coil, for electrical field intensity of a point at a depth of 1 mm on the hemisphere model, is shown in FIG. 15. Also, a relationship between distance from a surface of the coil center and strength of the magnetic flux density, when energization of 5.3 kA has been assumed as maximum output of a drive circuit, plotted for each coil, is shown in FIG. 16. Values and spread of an electrical field intensity that has been obtained using an SPFD method, and values of inductance that have been obtained using a finite element method, are shown in table 3.

TABLE 3

Comparison With Existing Coils

|  | FIG. 8 Coil | Dome Coil | Double-D Coil |
| --- | --- | --- | --- |
| Electrical Field Intensity (V/m) | 202 | 103 | 209 |
| Inductance (μH) | 9.7 | 12.9 | 8.2 |
| Total Winding Length (m) | 3.9 | 5.8 | 3.7 |
| Induced Electrical Field Spread (cm) | 6.0 × 3.3 | 9.7 × 5.3 | 8.8 × 4.7 |

In table 3 and FIG. 15, an average value for electrical field intensity in a calculation region is 202 V/m in the case of a figure 8 coil, but 209 V/m in the case of a Double-D coil, while a maximum value for induced electrical field at a point at a depth of 1 mm is 215 V/m for the figure 8 coil and 237 V/m for the Double-D coil. In this way, final design of the Double-D coil can achieve the same or better induced electrical field intensity compared to that of the existing figure 8 coil. In addition, as shown in FIG. 14, according to the coil of this example spread of the induced electrical field is large, and accordingly there is the advantage that the coil is resistant to mislocation. Inductance value is also kept to within 10 μH, which is preferable for connection to a generic drive circuit.

Also, in FIG. 16, magnetic field strength at a position 5 mm from the coil surface is 0.81 T for the figure 8 coil, but 0.63 T for the Double-D coil, and so magnetic flux density of the figure 8 coil is higher. However, while on the one hand magnetic field strength has the same value of 0.48 T for both coils at a distance of 16 mm from the surface, further, at a distance of 20 mm from the surface the magnetic flux density is 0.40 T for the figure 8 coil but 0.42 T for the Double-D coil, and so the level relationship for strength has switched.

What this specifically means is that generation efficiency of an induced electrical field at a position that is 16 mm or more from the coil surface is better for the Double-D coil than for the figure 8 coil. Since a stimulation point for a cerebral gray matter surface, over the scalp and the skull, and cerebral spinal fluid, is positioned at 15 mm or more from the coil surface, because of this characteristic the Double-D coil can be said to have an effective characteristic with respect to stimulation in the vicinity of a gray matter surface.

There are also the following two incidental advantages.

First, induced electrical field at the coil surface is preferably low. There are temporal muscles and thigh membranes in the vicinity of the scalp directly above the primary motor cortex, with these muscles moving with magnetic stimulation, and depending on the test subject there may be a problem of accompanying unpleasantness. Also, medical treatment is basically painless, but depending on the test subject there may be cases where sensory receptors of the skin are stimulated, and subject will complain of slight itching or the like. By making induced electrical field close to the coil surface small, there is the possibility of reducing these minor side effects.

As shown on the characteristic curve of the coil of this practical example that was plotted as the "Double-D" coil of FIG. 16 under the simulation conditions of this practical example that were shown previously, the coil of this practical example is constructed such that change rate of magnetic flux density at a stimulation point with respect to change in distance (mm) from the coil surface to the stimulation point becomes a change rate in the vicinity of 0.014 [T/mm] or a change rate that is read from FIG. 16, or less than these values, which means that it becomes possible to reduce unpleasantness caused by stimulation close to the scalp as well, at the time of treatment where an irradiation target within the brain is subjected to magnetic stimulation.

Conversely since the same change rate becomes close to 0.027 [T/mm] with the Figure-8 coil that was plotted as the Figure-8 coil in FIG. 16, the same effect as with a coil of this practical example cannot be expected with the figure 8 coil. Specifically, in a case where magnetic stimulation has been carried out to generate magnetic flux density of the same strength at a stimulation point within the brain, as is clear from FIG. 16, magnetic flux density close to the scalp, which is a position where distance from the coil surface is short, becomes a smaller value with the coil of this practical example than with a figure 8 coil, which means that even if unpleasantness arises that is attributable to performing stimulation close to the scalp, such unpleasantness is less than with the FIG. 8 coil.

It should be noted that a dome type coil that has been plotted as "Dome Coil" in FIG. 16 has a smaller rate of change than the coil of this practical example, but the magnitude of magnetic flux density generated under the design conditions of the dome type coil used in this comparative example is smaller than that of the coil of this practical example, and so in the case where it is used in medical practice stimulation intensity becomes small, and in order to ensure required stimulation intensity it is necessary to increase electrical current, namely, supplied power.

That is, the coil of this practical example is a coil for magnetic stimulation treatment that has been constructed such that a rate of change of magnetic flux density at a stimulation point with respect to distance (mm) from a coil surface to the stimulation point, when pulse current is applied at a maximum current of 5.3 kA and a pulse frequency of 3.4 kHz, becomes a change rate close to 0.014 [T/mm] or a rate of change read from FIG. 16, or less than these numerical values, and such that magnitude of magnetic flux density of the stimulation point becomes greater than or equal to 0.2 T.

Also, as a second point, induced electrical field of a portion that is deeper than a gray matter surface is preferably high (that is, being able to stimulate to a deep position is desirable). Gray matter is distributed within 5 mm from the surface of the brain, sulcus depth is also about 10 mm, and nerve groups of pyramidal cells of the motor area cortex that is stimulated for treatment are thought to be distributed from the outer surface of the brain to a depth of about 15 mm. There is an example, as treatment of depression, where a new shaped coil is being developed in order to stimulate the prefrontal area widely and deeply, and taking this into an account a higher treatment efficiency is thought to be highly possible by stimulating to a deep position.

Modified Example . . . Localization Technique for Stimulation Convergence that Combines Different Direction Laminated Cores The Double-D coil that has been described in this embodiment has sufficiently practical characteristics with respect to all of induced electrical field spread, electrical field intensity and inductance, but on the other hand since an induced electrical field is somewhat strongly generated using the connection parts 311b (namely the lateral conductors), as shown in FIG. 14, there is a possibility of an induced electrical field being unintentionally generated slightly in the brain region when actually carrying out magnetic stimulation. In order to resolve this, a magnetic stimulation device that uses a core member 33 (refer to FIG. 17) will be described as a modified example. It should be noted that in the description of this modified example, elements that are basically common to the previously described embodiment use the same reference numerals, for the purpose of simplifying description. Also, in this modified example, so-called different direction laminated cores (sometimes simply referred to as laminated cores, or cores) are used as the core member 33. Detailed structure of the core member 33 will be described later.

(Effect of Laminated Core on Magnetic Stimulation Spot)

First, the effects that the laminated cores have with regards to the transcranial magnetic stimulation coil will be described. There have been several studies in the past into improving electromagnetic stimulation efficiency by combining a ferromagnetic body with a TMS coil, from Han et al, to arrange a laminated core at the top of a circular coil (B. H. Han, S. Y. Lee, J. H. Kim, J. H. Yi, "Some technical aspects of magnetic stimulation coil design with the ferromagnetic effect," Medical & Biological Engineering & Computing, vol. 41(5), pp. 516-518, 2003). This has been expanded upon by Miyawaki et al, who reported being able to significantly improve electromagnetic stimulation effectiveness by combining laminated core plates in different directions with an eccentric figure 8 coil having improved locality (K. Yamamoto, Y. Miyawaki, Y. Saitoh, and M. Sekino, "Improvement in Efficiency of Transcranial Magnetic Stimulator Coil by Combination of Iron Core Plates Laminated in Different Directions," IEEE Transactions on Magnetics, vol. 52, 2016). This fundamental principle has the advantages that steel plates that have been laminated in a direction perpendicular to the conductors are successful in terms of the effectiveness of improving induced electrical field directly below the conductors, while conversely steel plates that have been laminated in a direction parallel to the conductors are successful in terms of the effectiveness of attenuating induced electrical field directly below the conductors by generating large loss current within the steel plates. Miyawaki et al increase induced electrical field at a center portion where it is desired to intensify stimulation by preparing steel sheets that have been laminated in a vertical direction for the outer side of an eccentric figure 8 coil and laminated in a horizontal direct at the inner side, and by making induced electrical field small at an outer edge portion where stimulation is not required, the effect is achieved of being able to optimally improve stimulation intensity.

With this modified example, learning from this result, the objective is to attenuate induced electrical field of the Double-D coil of this embodiment at points where stimulation is not necessary, and increase induced electrical field at a central portion, and verification is carried out for a model that combines a Double-D coil and laminated steel plates as the core member 33.

(Simulation Conditions)

Figure 17:
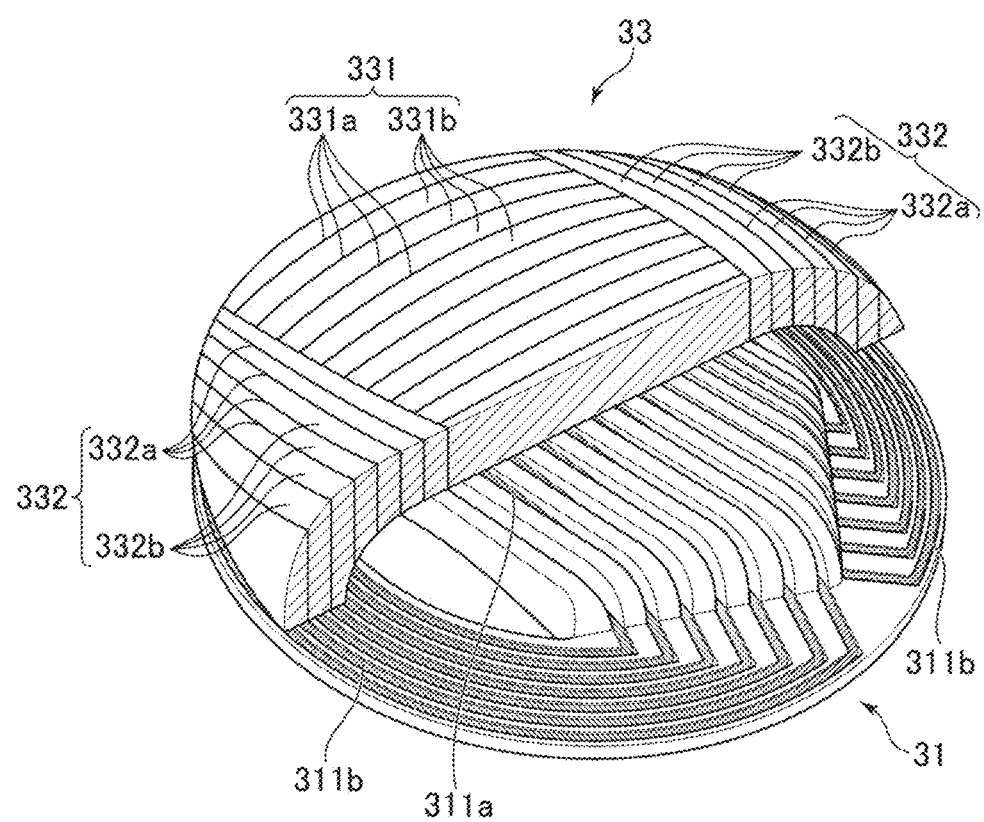
FIG. 17 is an explanatory drawing for describing a modified example of this embodiment, and is essentially a cross sectional drawing with only a core member shown in cross section, in a state where the core member is placed on the coil surface.
Figure 18:
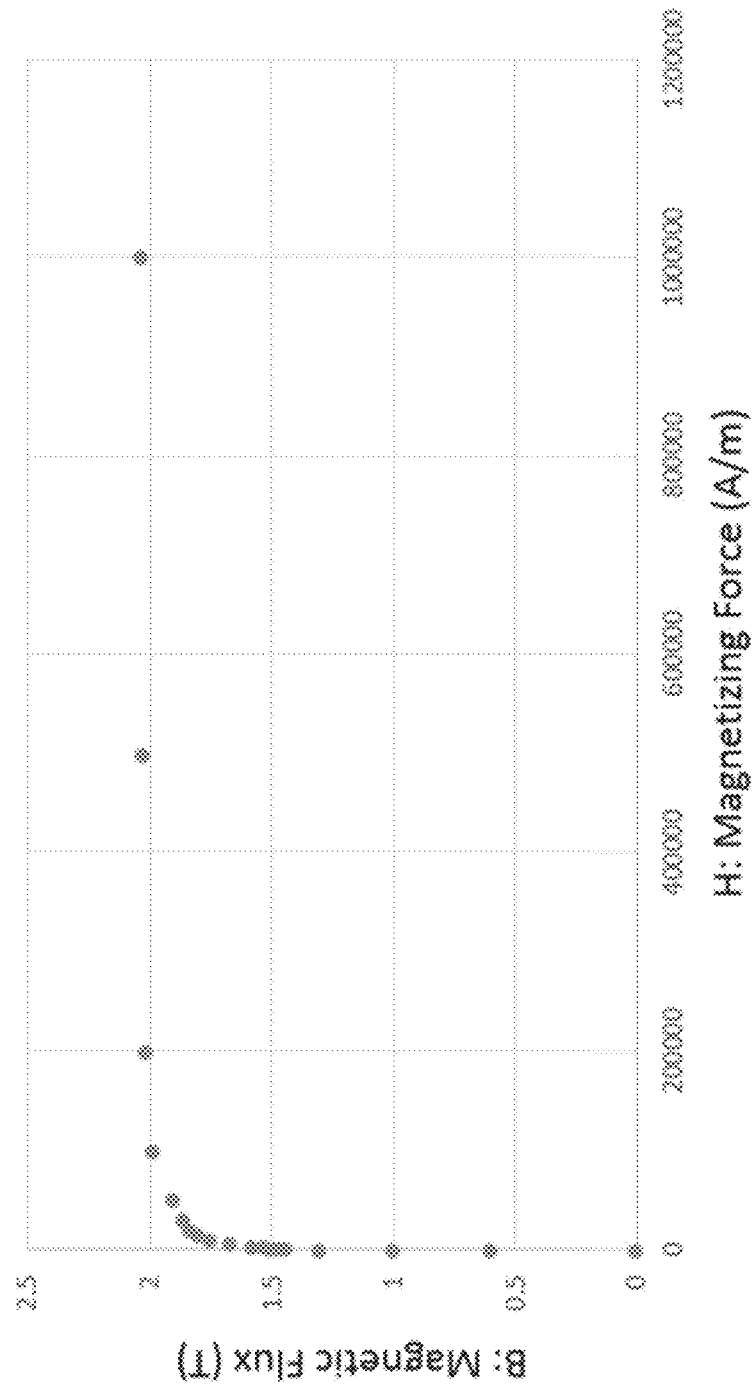
FIG. 18 is a graph showing setting examples of relative permeability of silicon steel sheets used in the core member, with the horizontal axis being magnetic field strength and the vertical axis being magnetic flux density.

Since it is necessary to simulate the effect of the steel plates, all calculation was carried out using finite element methods. The number of turns of the Double-D coil was made 14. The core member 33 was shaped so as to cover the entire coil, following the shape of the Double-D coil, as shown in FIG. 17. It should be noted that FIG. 17 shows appearance with only the core member 33 in cross-section. The conductor body hemisphere had a radius of 75 mm while the air region had a radius of 150 mm. Here, in order to accurately calculate and simulate magnetic flux that is generated peripherally by the coil, an air region having sufficient width was set. Conductivity of steel was made $10^7$ in a non-lamination direction, and made $10^{-7}$ in the lamination direction. Relative permeability was set nonlinearly, as shown in FIG. 18, on the assumption that there is saturation at a maximum magnetic flux density of about 2 T, assuming silicon steel sheets. Steel thickness was made 5 mm. Using the conductor skin effect, from equation (4) below, if $\sigma=10^7$ S/m and f=3.15 kHz are set, penetration of magnetic flux is considered to be only to a depth of 40 μm, and this thickness of 5 mm is sufficiently large for this depth. The lamination directions are set so that portions 44 mm from the center of the core member 33 have steel plates ( . . . corresponding to first core bodies 331a) in an alignment direction (lateral direction) perpendicular to conductors (actuation parts 311a), and outside this portion steel plates ( . . . corresponding to second core bodies 332a) are in an alignment direction that is parallel to the conductors (vertical direction). Current that flows in the coil is set to 5.3 kA, at a frequency of 3.15 kHz. Portions 331b between the first core bodies 331a and portions 332b between the second core bodies 332a are composed of a material having a low relative permeability.

$$\delta = \frac{1}{\sqrt{\pi\sigma\mu f}} \quad (4)$$

(Results and Observations)

Figure 19:
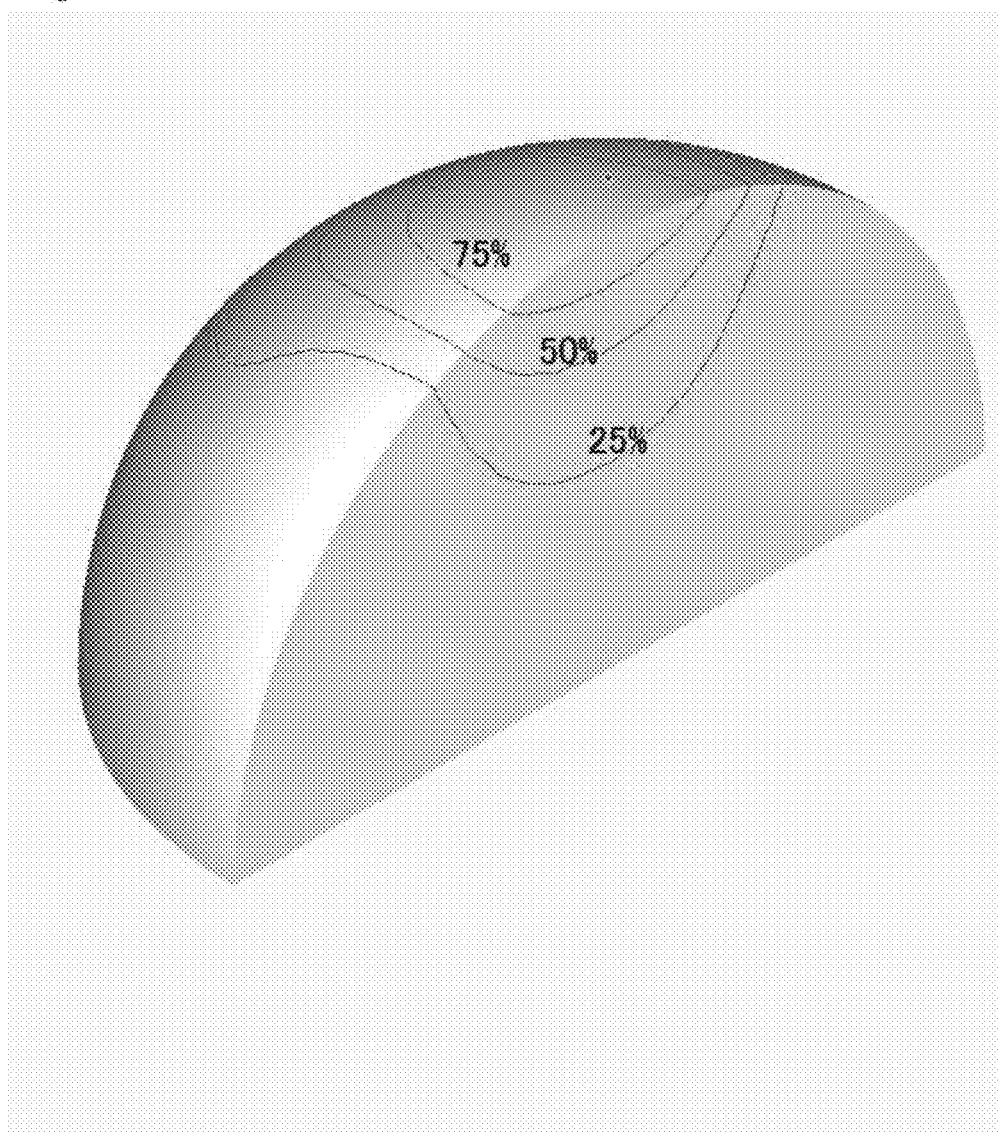
FIG. 19 is an explanatory drawing showing appearance of an induced electrical field obtained by simulation using the core member.
Figure 20:
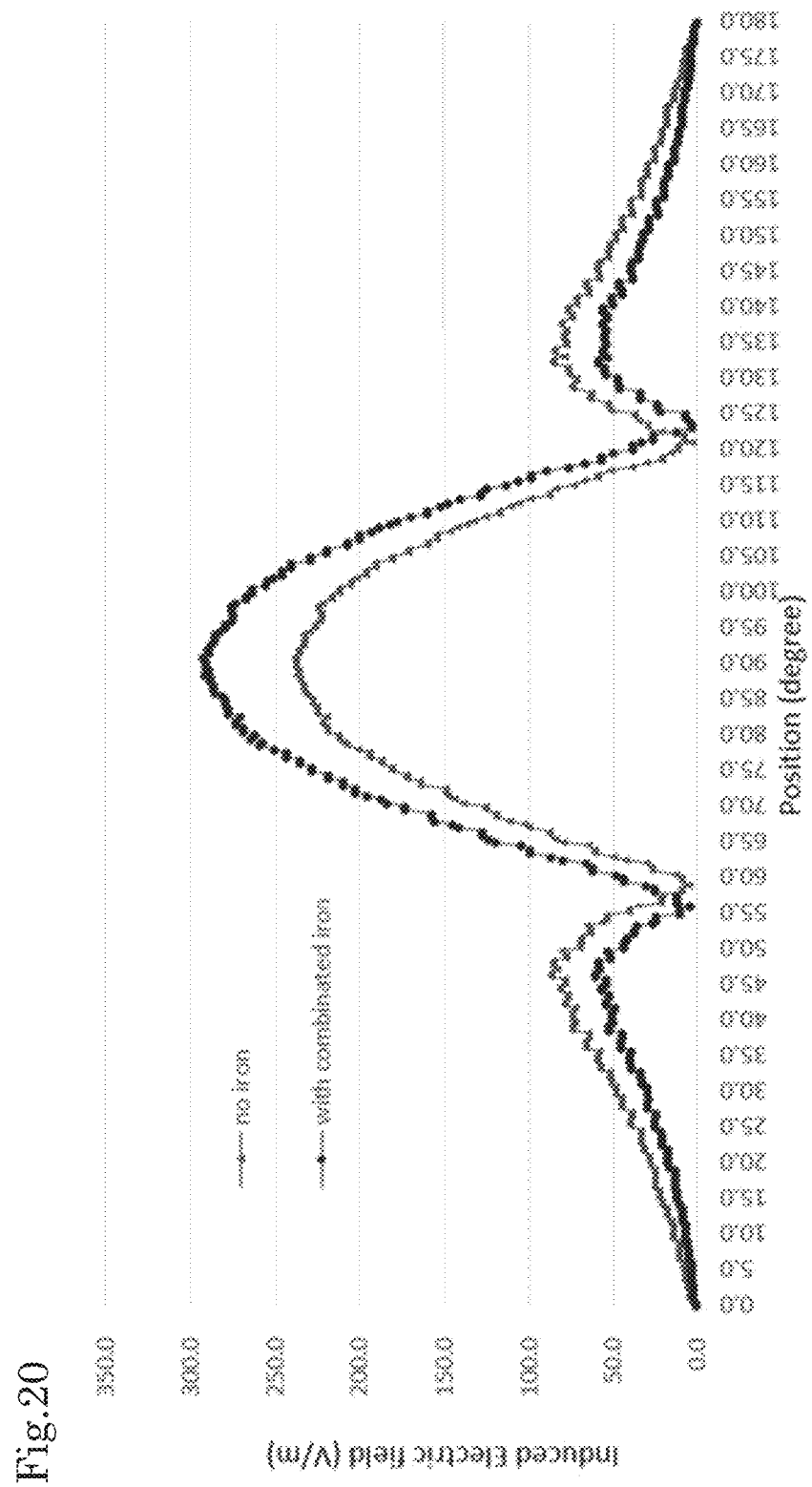
FIG. 20 is a graph for describing characteristics of a coil using the core member, with the horizontal axis being measurement position (rotational angle about the coil center) and the vertical axis being induced electrical field intensity.

Appearance of the obtained induced electrical field is shown in FIG. 19. Also, intensity of the induced electrical field at the depth of 1 mm from the hemisphere surface is shown in FIG. 20. The first peak (portion corresponding to directly below the side conductors (connection parts 311b) of the Double-D coil) of induced electrical field intensity in FIG. 20 was 86.6 V/m in the case where horizontal direction steel plates in different directions were not arranged, but 60.2 V/m in a case where steel plates were arranged. Also, maximum intensity of the induced electrical field generated at the center, as a second peak, was 238.7 V/m in the case where steel plates were not arranged, and 292.0 V/m in the case where steel plates were arranged. Inductance value was 1904 μH if the core members (laminated steel) were arranged, compared with 7.4 μH when there were no core members.

As a result of this, for a Double-D coil also it is possible to cleverly suppress induced electrical field at points where stimulation is not necessary by using laminated steel plates in different directions, and it is possible to significantly improve electrical field intensity at the stimulation center point. However, since inductance value is extremely large, it is not considered possible to connect to a normal drive circuit. In order to avoid this situation it is considered necessary to make the steel plates smaller and thinner with the intention of lowering the inductance value. Otherwise, it will be necessary to assume use of a practical drive circuit that can arbitrarily change wavelength regardless of value of inductance, as proposed by Peterchev et al (A. V. Peterchev, R. Jalinous, and S. H. Lisanby, "A Transcranial Magnetic Stimulator Inducing Near-Rectangular Pulses With Controllable Pulse Width (cTMS)," IEEE Transactions on Biomedical Engineering, vol. 55, 2008, pp. 257-266).

The device of the modified example can be realized as follows.

(A1)

A coil in which the core member 33 is constructed to reduce magnetic resistance of a magnetic circuit generated by the 1st to Nth turns, and the core member is arranged at a position opposite to an object 1 over actuation parts 311a.

(A2)

A coil as described in item A1, in which the core member 33 is characterized by having a plurality of regions (331a, 331b, 332a, 332b) of differing relative permeability.

(A3)

A coil as described in item A1 or A2, in which the core member 33 is provided with a first portion 331 arranged at a position that faces the actuation parts 311a, and a second portion 332 that is arranged at a position that faces the connection parts 311b, the first portion 331 being provided with a plurality of elongated first core bodies 331a that extend in a direction non-parallel (or orthogonal) to the actuation parts 311a, and the second portion 332 being provided with a plurality of elongated second core bodies 332a that extend in a direction that is substantially parallel to the extension direction of the actuation parts 311a.

Practical Example 2 . . . Characteristic Evaluation by Measurement

With practical example 2, for a Double-D coil of 14 turns and inner diameter width of 14 mm that was explained as an embodiment, actual manufacture was carried out, and results of having carried out energization and measurement experiments are shown. With this practical example 2, as conductors for constituting the coil 31 two ply tin-coated copper wire mesh having a thickness of 0.8 mm and a height of 4 mm was used, and this was fitted into grooves on the surface of the support 32. Effective cross-section of the conductors became 3.4 mm$^2$. By using this type of two-ply copper wire mesh it can be wound easily, and it is possible to lower a centroid of a current path.

Results are shown in table 4 below.

TABLE 4

| Inductance measurement values (μH) at 1 kHz | | | |
|---|---|---|---|
| Coil Type | Double-D Coil | FIG. 8 Coil | Circular Coil (C100) |
| Inductance | 10.3 | 12.1 | 9.6 |

Inductance of the coil of this embodiment was 10.3 μH. A commercially available circular coil (circular coil C100 by the MagPro company) was 9.6 μH, while a figure 8 coil was 12.1 μH. As a result of this, the coil of this embodiment has an inductance characteristic substantially the same as that of an existing coil, and it will be understood that it is applicable to an existing power supply.

(Static Magnetic Field Measurement when Energizing Direct-Current)

A maximum value of magnetic flux density that has been generated by a drive circuit can be approximated to a value of magnetic flux density at a static magnetic field that has been generated by direct-current. This means that it is possible to predict magnetic flux density at the time of drive by measuring a static magnetic field when a direct current has been applied to the coil. Here, as a preliminary experiment before energization using the drive circuit, direct current was made to flow in the coil of this embodiment and a figure 8 coil which was for the purpose of comparison, and the static magnetic field that is generated was measured.

(Experimental Conditions)

Based on the fact that the coil itself has parasitic resistance, measurement was carried out with the coil directly connected to a constant current source. A power supply used was PAR18-6A by the TEXIO company. GM07 by the HIRST magnetic Instruments company was used as a Gauss meter for static magnetic field measurement.

(Results and Observations)

Figure 21:
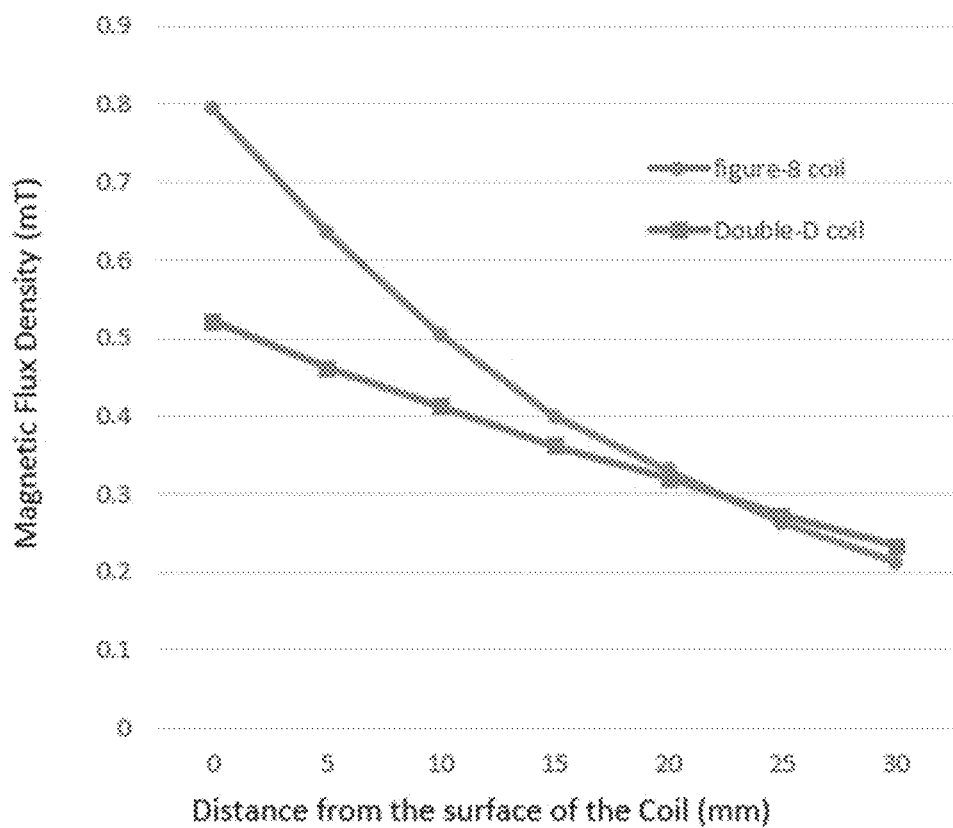
FIG. 21 is a graph that compares, using measurement, various conventional coils with the coil of this embodiment, with the horizontal axis being measurement position (distance from coil in the object direction (lower surface direction)) and the vertical axis being magnetic flux density.

Results are shown in FIG. 21. Magnetic flux density generated by a fixed current of 5 A was a higher value with the figure 8 coil in a region from 0 mm to 20 mm from the coil surface. On the other hand at points further than 20 mm away from the coil surface the Double-D coil generated a stronger magnetic field than the figure 8 coil. It should be noted that a value of magnetic flux density at a point 20 mm from the coil surface was 0.33 mT with the figure 8 coil and 0.32 mT with the Double-D coil.

Based on these results, if it can be considered that a distance from the surface of the scalp to the gray matter surface is on average about 20 mm, and it will be understood that stimulation intensity on gray matter nerves groups using the Double-D coil is about the same as that for the figure 8 coil. This more or less coincides with the simulation results of FIG. 16. However, considering the fact that in the simulation the magnetic flux density using the Double-D coil becomes higher than with the figure 8 coil at the point beyond 16 mm of the distance, there are some errors. This is thought to be due to slight differences between simulation models and real machines.

(Measurement of Applied Current and Varying Magnetic Field Using Real Drive Circuit)

A manufactured Double-D coil was connected to a commercially available drive circuit, and energization tests and varying magnetic field measurements were carried out.

(Experimental Conditions)

A MagProCompact by the MagVenture company was used in the drive circuit. A current monitor 4418 by the PEARSON Electronics was used as a current meter, an oscilloscope was connected, and a current waveform was stored. A search coil of outer diameter 7.6 mm and 6 turns (effective surface area 272 mm$^2$) is formed, positioned above a coil and connected to an oscilloscope, and then a magnetic filed thereof is measured by recording its waveform of instantaneous magnetic flux density. Position of the search coil is at the center of the figure 8 coil or Double-D coil, and measurement points were obtained every 5 mm up to a distance of 30 mm, with 0 mm as an attachment part. In addition to this, an integrated value of up to a ¼ period of the obtained instantaneous magnetic field was obtained as a maximum value of magnetic flux density, and after that the drive current value was normalized to a maximum value of 1 kA and comparison was carried out.

(Result 1 and Considerations-Current Waveform at the Time of Energization)

Figure 22:
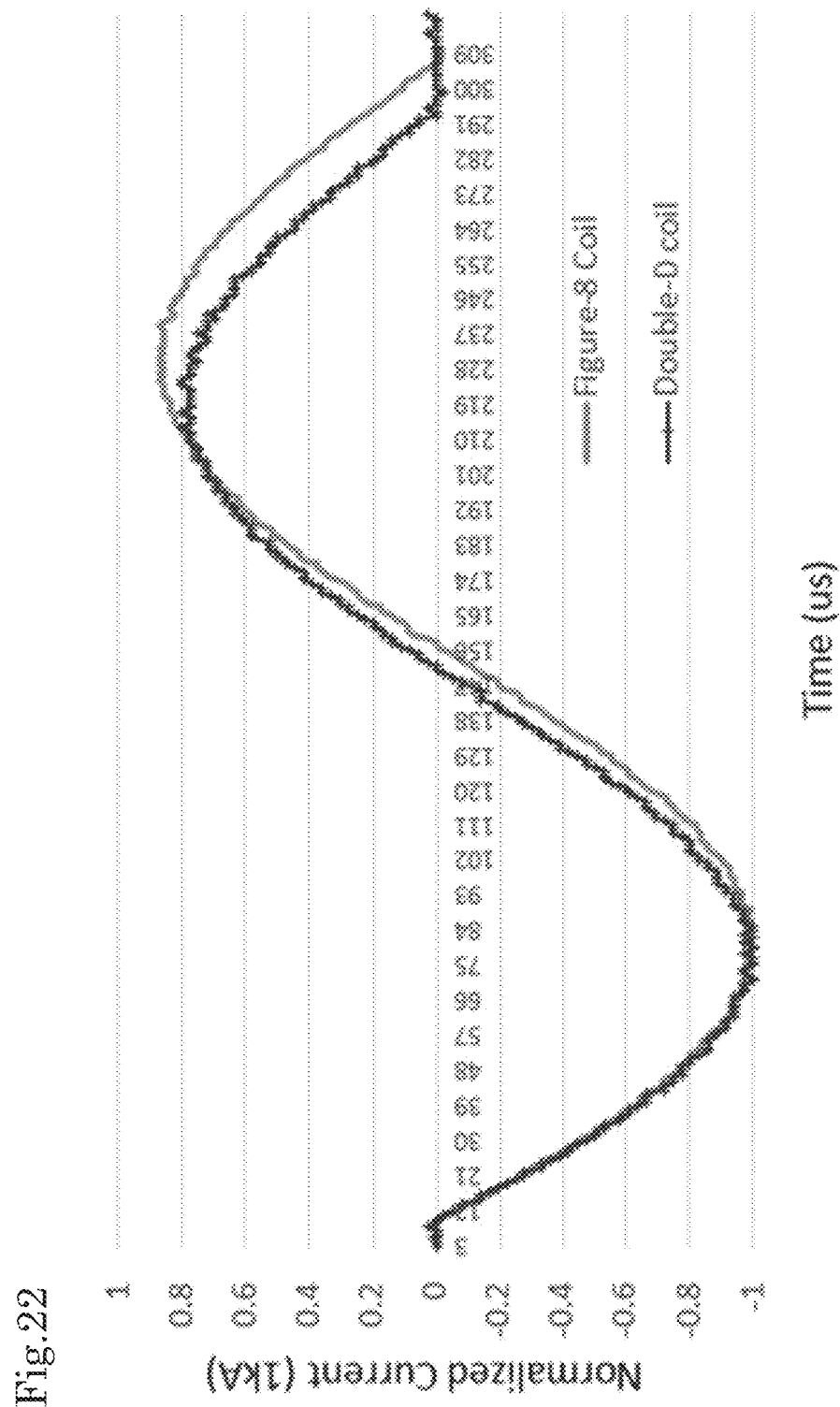
FIG. 22 is a graph showing a current waveform of a coil, using measurement, with the horizontal axis being time (μs) and the vertical axis being current value.

At the time of measurement, current amplitude of the FIG. 8 coil was 1.9 kA while current amplitude of the Double-D coil was 1.4 kA. Current waveforms for the figure 8 coil and the Double-D coil that have had current amplitude normalized to 1 kA are shown in FIG. 22. Current wavelength using the FIG. 8 coil was 295 μs, while wavelength using the Double-D coil was 283 μs. Also, regarding attenuation due to parasitic resistance of the coils, making an absolute value of a first peak of the respective amplitudes 1, a second peak value is 0.875 with the figure 8 coil and 0.806 with the Double-D coil.

Regarding wave length, the Double-D coil can generate triphasic pulses of the same waveform as the figure 8 coil, and as a result of measurement taking into account inductance value, a wavelength of shorter than 300 μs was obtained. As a result of this, from the viewpoint of wavelength, stimulation of cranial nerve is certainly possible.

It is also possible to obtain a value of parasitic resistance R from attenuation of a current waveform. If a first peak value is made $I_1$ and a second peak value is made $I_2$, resistance R of an RLC series circuit is represented as shown below.

$$R = \frac{L}{T}\left(1 - \left(\frac{I_2}{I_1}\right)^4\right) \quad (5)$$

Here, T is current wavelength, and is represented by $T=2\pi \times \sqrt{(LC)}$.

Also,

L: circuit inductance, and

C: circuit capacitance.

If the inductions that has been measured here and the wavelength that has been acquired are substituted, then the resistance of the figure 8 coil becomes 17.0 mΩ), and the resistance of the Double-D coil becomes 21.0 mΩ). The reason for this is that with the Double-D coil, while length of the winding is equal to that of the figure 8 coil, a mesh conductor having a small cross sectional area is used as the winding. Due to the fact that the parasitic resistance value is high there is a concern that coil heating at the time high-frequency continuous energization will take place rapidly, and improvement that would tend to increase cross-sectional area of the winding is considered preferable. Since with a Double-D coil the size can be made comparatively smaller for applying current for imparting the same induced electrical field intensity to gray matter as described previously, it can be predicted that effective heating rate will be of about the same extent. It is also considered that a Double-D coil would exhibit sufficient performance for at least single nerve stimulation due to the fact that a waveform is close to that of an existing coil with attenuation not being so large.

(Result 2 and Considerations-Wave Form of Instantaneous Magnetic Flux Density at the Time of Energization, and Maximum Magnetic Flux Density Value)

Figure 23:
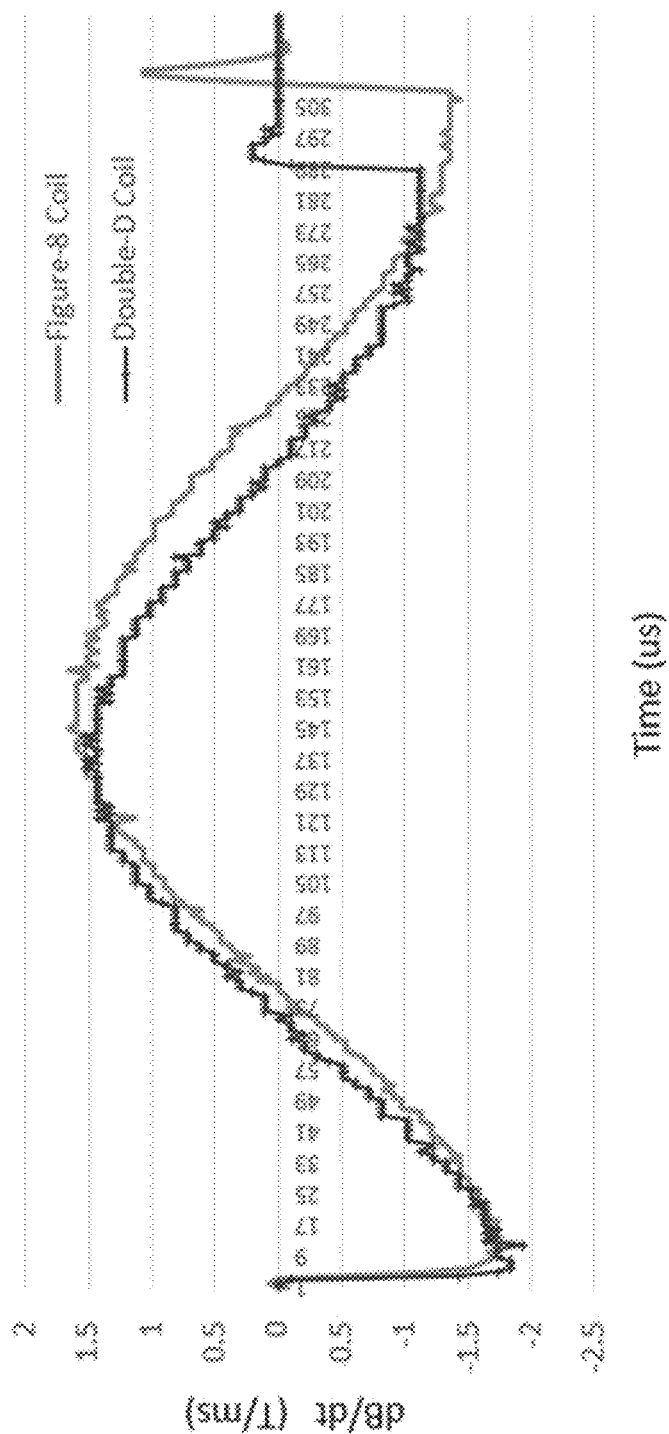
FIG. 23 is a graph showing instantaneous magnetic field of a coil, using measurement, with the horizontal axis being time (μs) and the vertical axis being instantaneous magnetic field.
Figure 24:
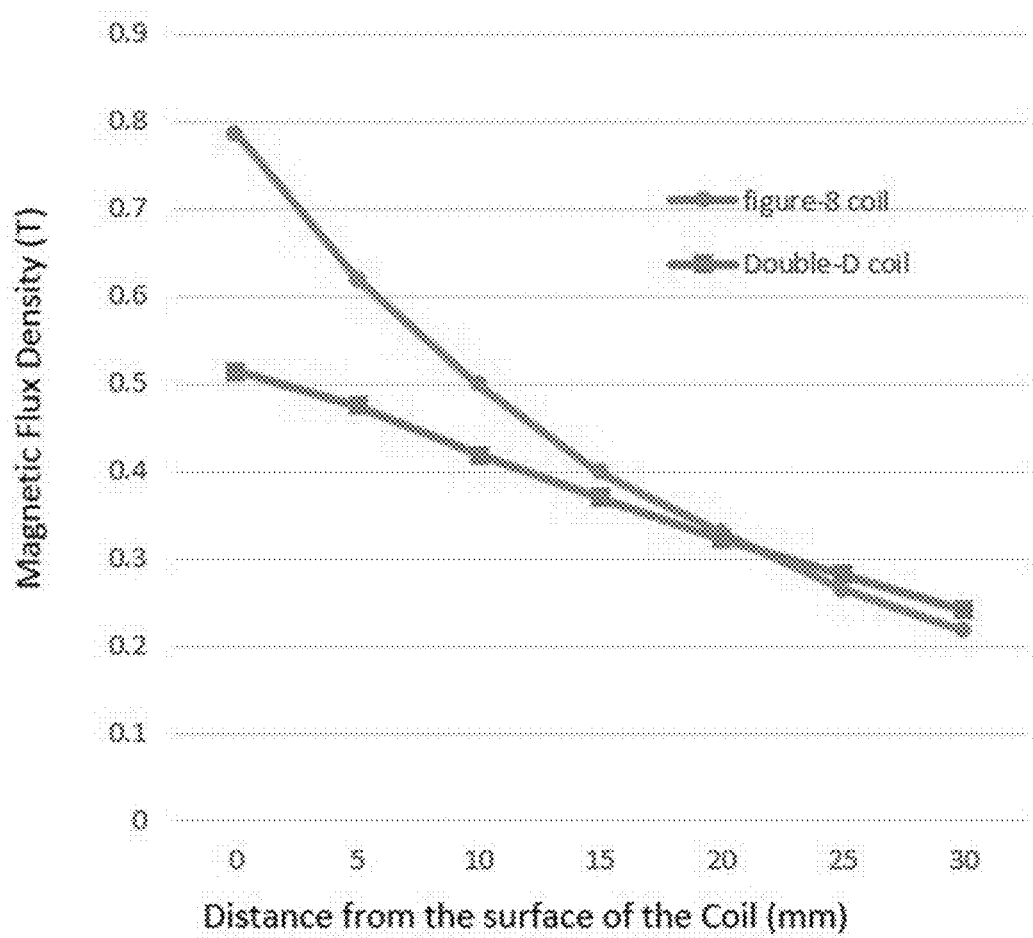
FIG. 24 is a graph that compares a conventional figure 8 coil with the coil of this embodiment, with the horizontal axis being measurement position (distance from coil in the object direction (lower surface direction)) and the vertical axis being magnetic flux density.

Waveforms for instantaneous magnetic field (dB/dt) at a position 15 mm from the surface of the figure 8 coil and the Double-D coil, that have been normalized based on an energization of 1 kA, are shown in FIG. 23. As shown in the drawing, an instantaneous magnetic flux density of the same intensity as that of the figure 8 coil was acquired. As a result of this, from the viewpoint of magnetic field strength, stimulation of cranial nerves is certainly possible. Also, with respect to distance from the coil surface, values of magnetic flux density obtained from strength of the instantaneous magnetic field that have been subjected to constant multiplication, so as to be equivalent to the case for 5 kA, are shown in FIG. 24. This result is a result that substantially coincides with the simulation of FIG. 16, and shows that it is possible to obtain induced electrical field of the same intensity as a figure 8 coil with a Double-D coil. An extremely close result has also been obtained in measurement with a static magnetic field. Strictly speaking, similarly to the case of static magnetic field measurement, a position from the surface at which magnetic flux density of the Double-D coil becomes stronger than for the figure 8 coil was 17 mm with simulation but 20 mm with actual measurements, meaning there was slight discrepancy. This is due to differences in dimensions etc. of a simulation model and actually manufactured devices, and can be assessed as not a fundamental issue.

(Supplementary Matters)

In the following, the original simulation software that has been used for validation of the previously described embodiments will be described. With this software, coil shapes have been input as collections of current vectors, making it possible to obtain induced current that will be generated in an electrical conductor. By incorporating brain MRI image data into the simulation it is also possible to carry out simulations for models where configurations are complex, such as when a plurality of type of conductors are included.

A general outline will first be given here of the principle of this software. With SPFD methods, objects that cause generation of an induced electrical field using a varying magnetic field are divided into micro-rectangular cuboids, and it is possible to obtain induced electrical field generated in each microvolume as a solution of difference equations for magnetic vector potential (T. W. Dawson and M. A. Stuchly, "Analytic validation of a three-dimensional scalar-potential finite-difference code for low-frequency magnetic induction," Applied Computational Electro-magnetics Society Journal, Vol. 16, pp. 63-71, 1996). First, if electric field E generated by a coil is represented using a magnetic vector potential $A_0$ and a scalar potential $\phi$, it becomes as follows.

$$E = -\frac{\partial A_0}{\partial t} - \nabla \phi \quad (6)$$

Also, using current continuous equations and Ohm's law, the following equations are established for induced current density J, and electric field E and conductivity σ.

$$\nabla \cdot J = \nabla \sigma E = 0 \quad (7)$$

The following equation is established from the two equations above.

$$-\nabla(\nabla \sigma \phi) = \nabla\left(\frac{\partial A_0}{\partial t}\right) \quad (8)$$

Here a minute hexahedron is assumed, with Sn being conductance of each straight line, ln being length of each straight line, φn being a scalar potential of a node n, and $A_{0n}$ being a magnetic vector potential of a direction component that joins a node 0 and a node n. If the above equations are discretized, the following equations are established for these values.

$$\sum_{n=1}^{6} S_n \phi_n - \left(\sum_{n=1}^{6} S_n\right) \phi_0 = \sum_{n=1}^{6} (-1)^n S_n l_n \frac{\partial A_{0n}}{\partial t} \quad (9)$$

By solving this equation for all voxels, it is possible to obtain an induced electrical field.

As has been described above, according to the coil of this embodiment, and an magnetic stimulation device that uses this coil, there is an advantage in that is possible to provide a coil that can give the same wide induced electrical field as a dome type coil, and that can generate a strong induced electrical field with the same applied current as for a dome type coil, and that can further keep inductance to a small value.

Second Embodiment

Figure 25:
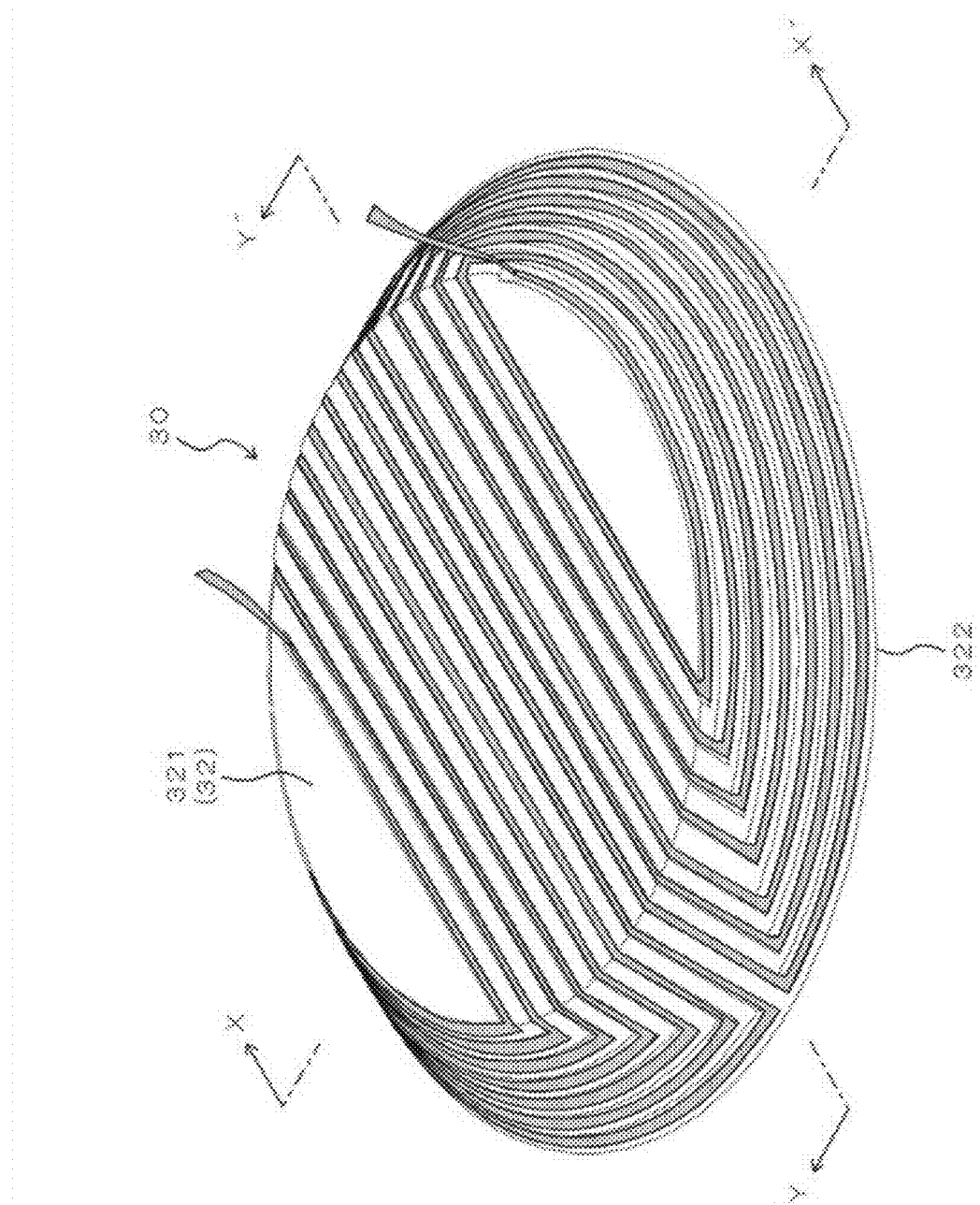
FIG. 25 is a schematic perspective view of an application part used in a magnetic stimulation device of a second embodiment of the present invention.
Figure 26:
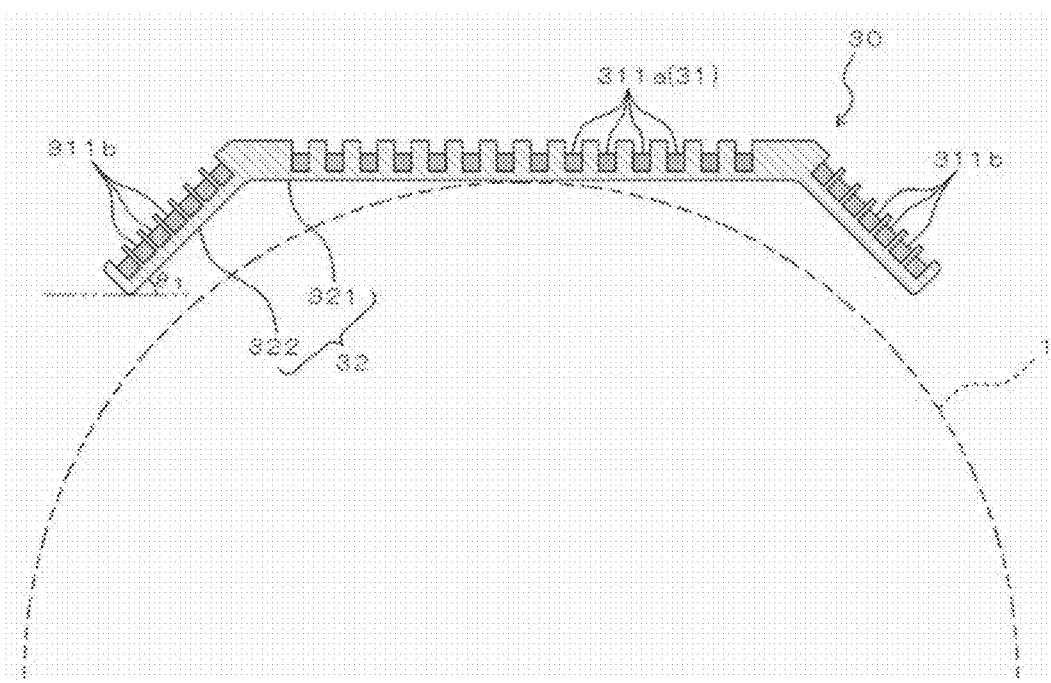
FIG. 26 is a horizontal cross sectional drawing taken along line X-X' in FIG. 25.
Figure 27:
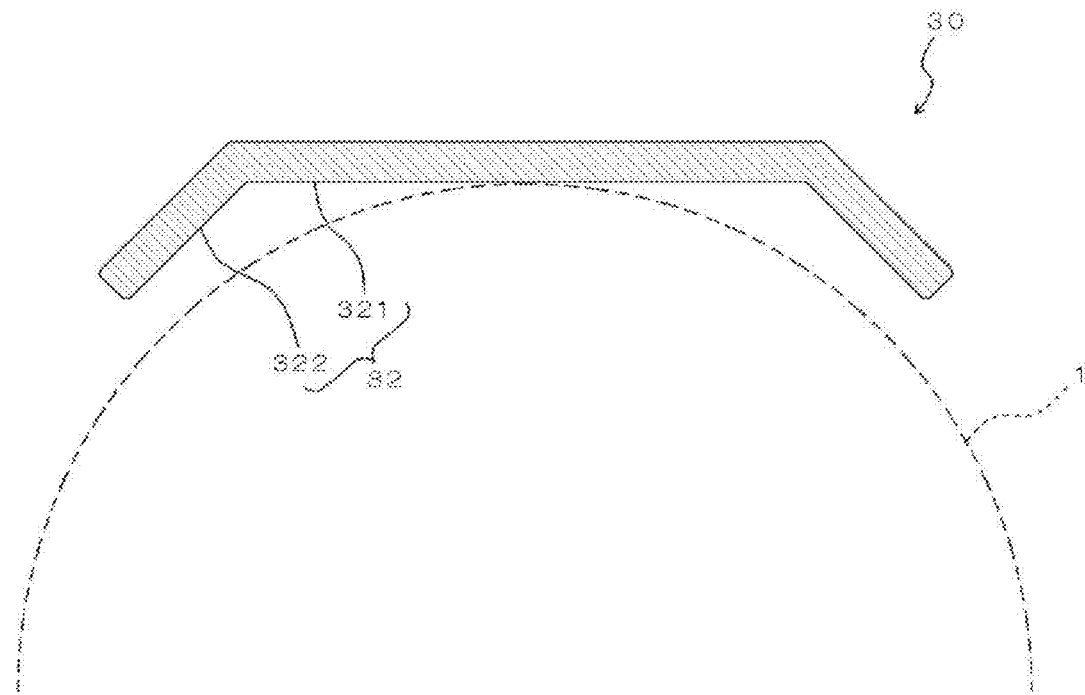
FIG. 27 is a vertical cross sectional drawing taken along line Y-Y' in FIG. 25.

Next, a magnetic stimulation device of a second embodiment of the present invention will be described with reference to FIG. 25 to FIG. 27. It should be noted that elements that are basically common to the magnetic stimulation device of previous embodiments that have already been described will be assigned the same reference numerals, to avoid duplicated description.

With the magnetic stimulation device of this embodiment, a contact section 321 constituting a support 32 of the application part 30 is configured so as to be substantially flat and circular. A flange section 322 is formed extending from a peripheral edge of the contact section 321 so as to be inclined towards the head 1 (refer to FIG. 26 and FIG. 27).

In a case where a bottom surface of the contact section 321 was made the spherical surface, as shown in FIG. 6, then in the event that curvature of the head 1 was smaller than the curvature of the bottom surface of the contact section 321 (that is, in the event that a contact surface for the head 1 approaches a planar surface), a phenomenon known as "partial contact" may sometimes arise. This is a state where although one side of a lower peripheral edge of the support 32 is contacting the head 1, the other side is separated from the head 1. In this state it is not possibly to set a positional relationship between the coil 31 and the head 1 according to expectations, and there is a possibility that it will not be possible to demonstrate the intended effect.

With this second embodiment, therefore, this problem is dealt with by making a bottom surface shape of the contact section 321 (that is, the shape of the bottom surface of the support 32) close to a planar surface (namely flattening). With this embodiment, when fitting the application part 30 to the head 1, the bottom surface of the contact section 321 is brought into contact with the surface of the head 1. In this way, it is possible to closely contact and position the vicinity of the center of the contact section 321 on the head 1. As a result, with this embodiment there is the advantage that it is possible to set a positional relationship between the coil 31 and the head 1 as intended, and it is possible to carry out desired magnetic stimulation. Here, with this second embodiment, the upper surface shape of the contact section 321 on which the actuation parts 311a are arranged is also flattened. In this way, the actuation parts 311a of this embodiment are in a state of being arranged in a direction substantially along a tangential surface of the object 1, at contact points of the contact section 321 with the object (head) 1. In the event that a surface of the object 1 is a substantially spherical surface shape, the contact section 321 and the object 1 contact at a single point (including a case where this is a surface of a minute region), and at least in the vicinity of this contact point, this tangential surface has a surface that approximates to the surface shape of the object 1.

Figure 28:
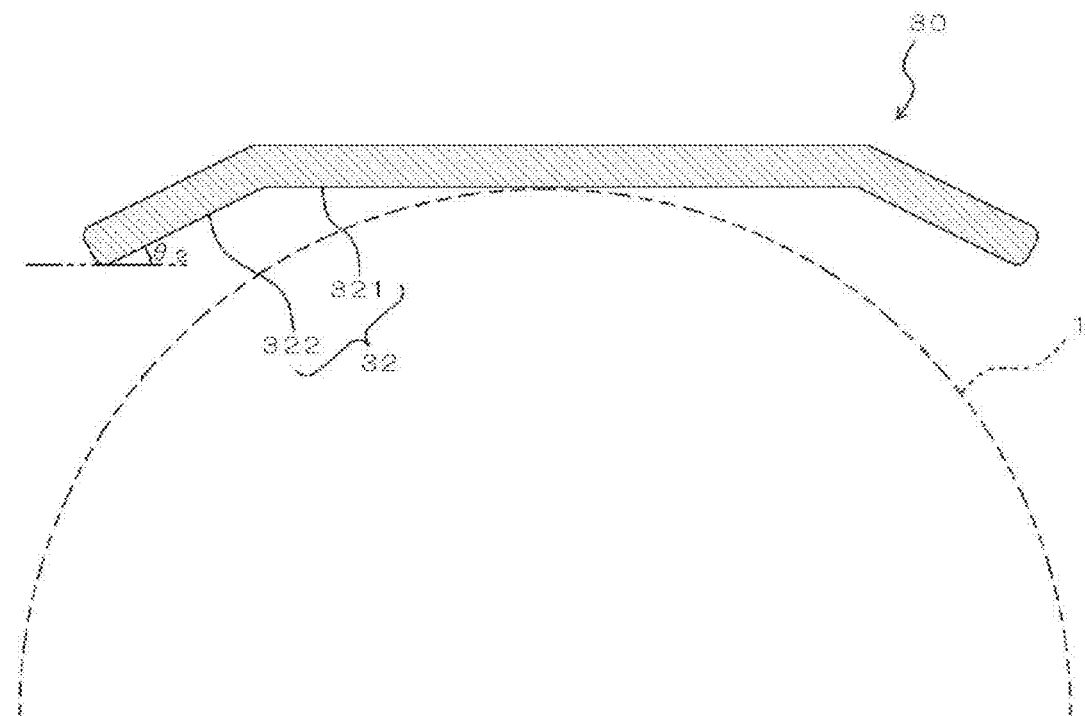
FIG. 28 is an explanatory drawing showing a modified example of the application part shown in FIG. 25, and is a cross sectional drawing at a position corresponding to FIG. 27.

A modified example of the device of this second embodiment is shown in FIG. 28. With the above described second embodiment, an angle formed by the contact section 321 and the flange section 322 is constantly made angle θ1 (refer to FIG. 26) over the entire periphery of the contact section 321. The angle θ1 in FIG. 26 is an angle formed by the contact section 321 and the flange section 322 in the direction X-X' in FIG. 25. By contrast, with this modified example, if an angle formed by the contact section 321 and the flange section 322 in the direction Y-Y' is made θ2, then θ1>θ2. Specifically, with this modified example, an angle formed by the contact section 321 and the flange section 322 differs depending on the location. In this way, with this modified example, there is the advantage that when fitting the support 32 to the head 1, it is possible to reduce the possibility of interference between the flange section 322 and the head 1.

Other structures and advantages of this second embodiment are the same as those of the previously described embodiment, and so more detailed description has been omitted.

Third Embodiment

Figure 29:
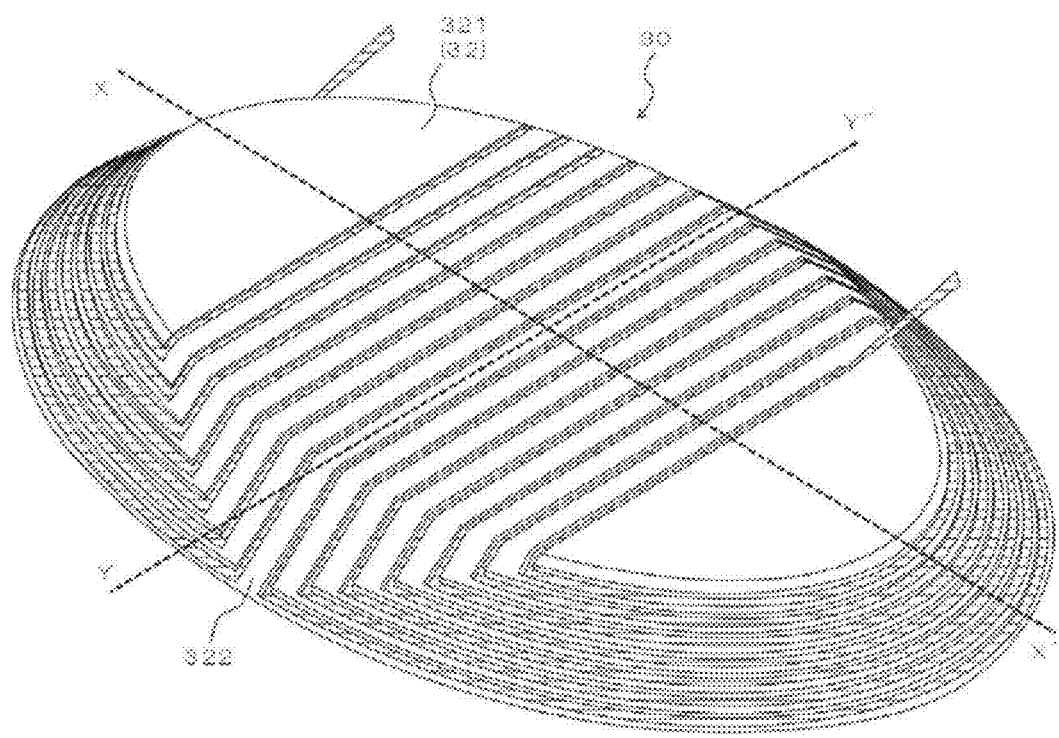
FIG. 29 is a schematic perspective view of an application part used in a magnetic stimulation device of a third embodiment of the present invention.
Figure 30:
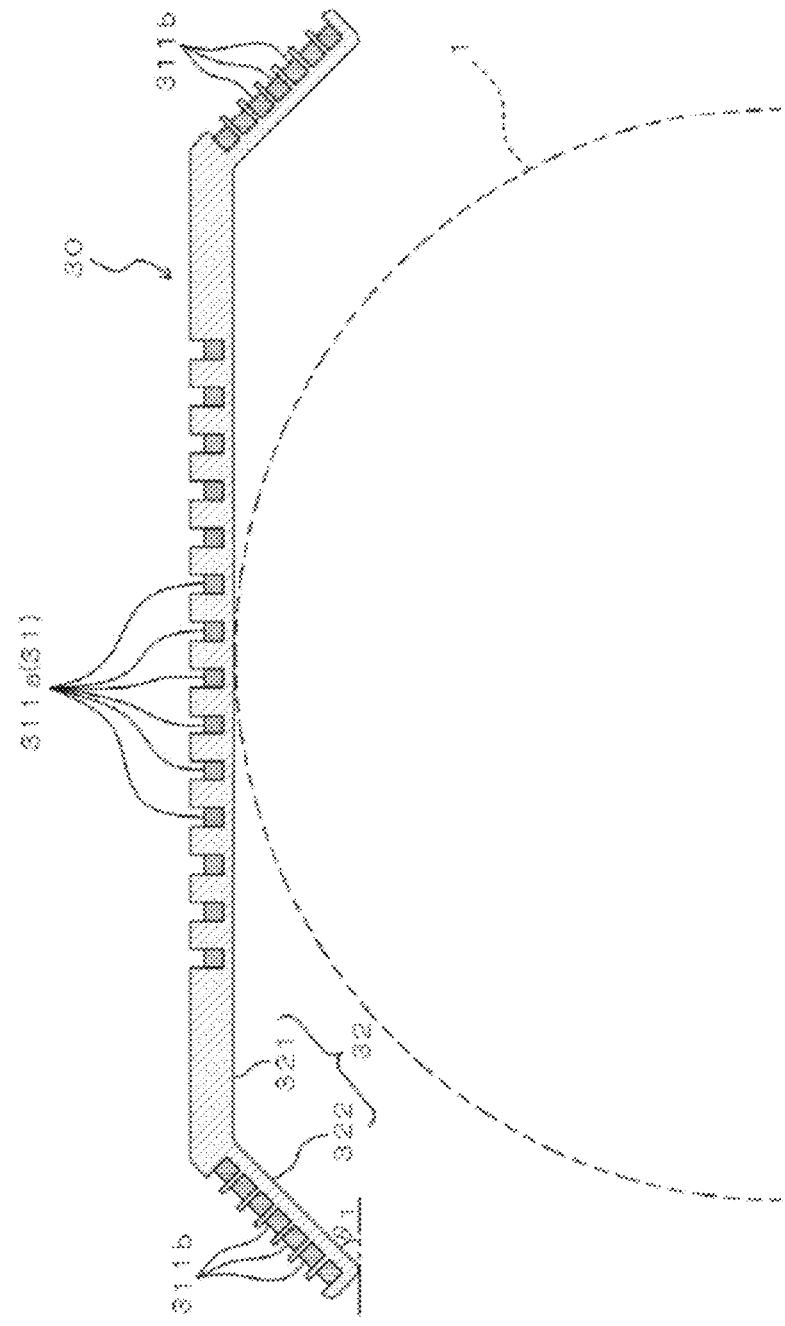
FIG. 30 is a horizontal cross sectional drawing taken along line X-X' in FIG. 29.
Figure 31:
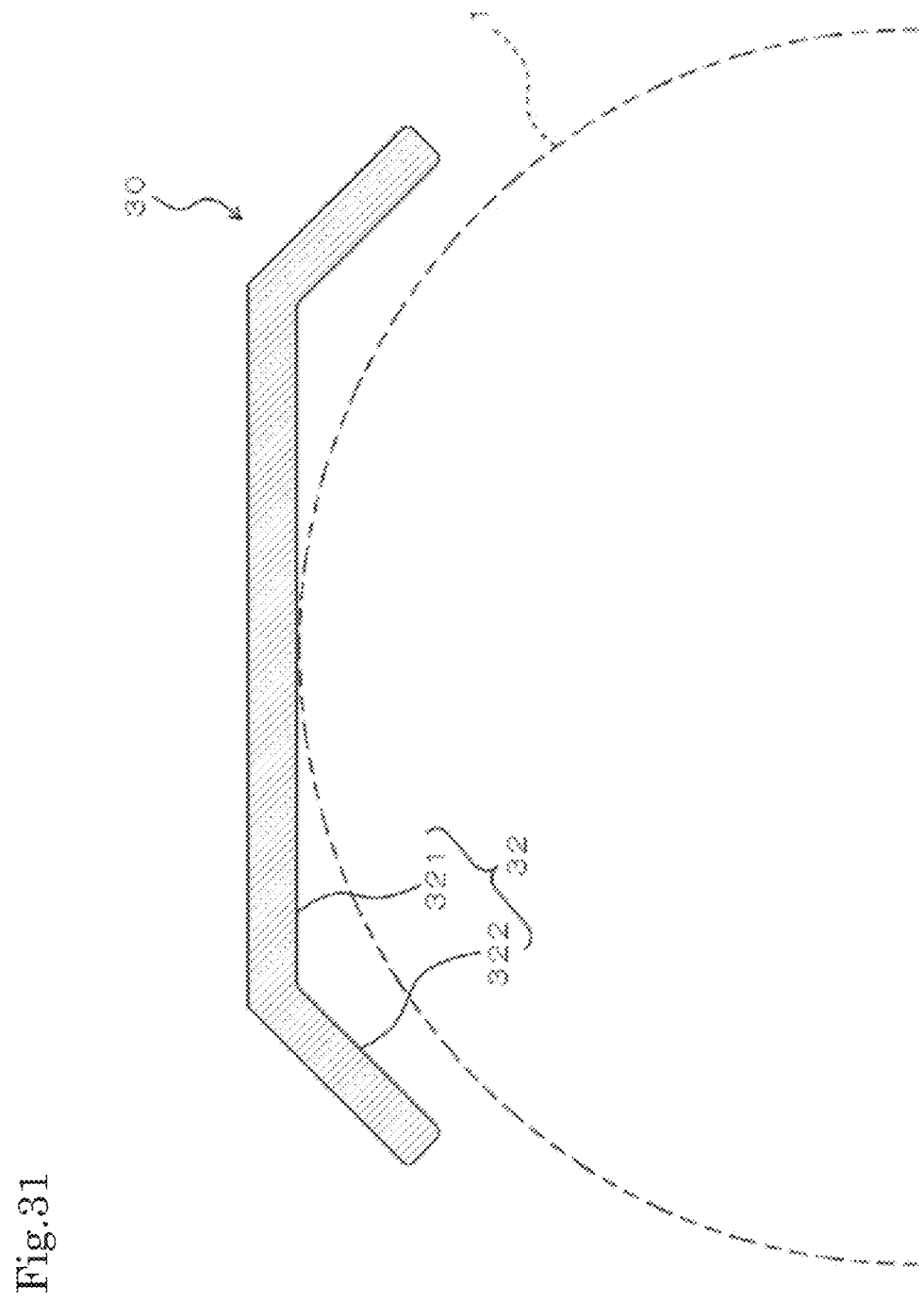
FIG. 31 is a vertical cross sectional drawing taken along line Y-Y' in FIG. 29.

Next, a magnetic stimulation device of a third embodiment of the present invention will be described with reference to FIG. 29 to FIG. 30. It should be noted that elements that are basically common to the magnetic stimulation device of the second embodiment that has already been described will be assigned the same reference numerals, to avoid duplicated description.

With the magnetic stimulation device of this embodiment, a contact section 321 constituting a support 32 of the application part 30 is configured so as to be substantially flat and elliptical.

Figure 32:
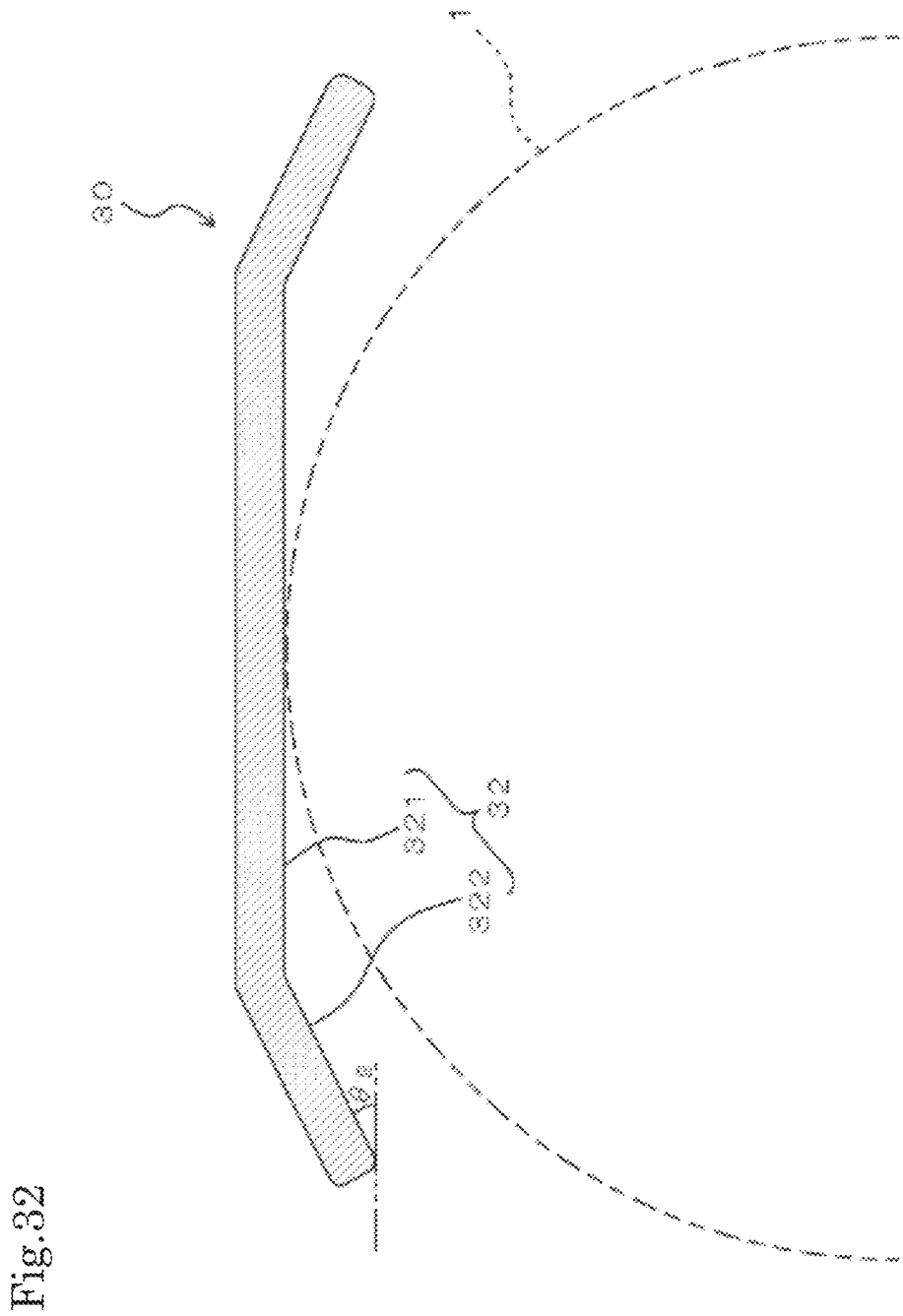
FIG. 32 is an explanatory drawing showing a modified example of the application part shown in FIG. 29, and is a cross sectional drawing at a position corresponding to FIG. 31.

A modified example of the device of this third embodiment is shown in FIG. 32. With the above described third embodiment, an angle formed by the contact section 321 and the flange section 322 is generally made angle θ1 (refer to FIG. 30). Conversely, with this modified example, this angle differs with position such that θ1>θ2.

Other structures and advantages of this third embodiment are the same as those of the previously described second embodiment, and so more detailed description has been omitted.

Fourth Embodiment

Figure 33:
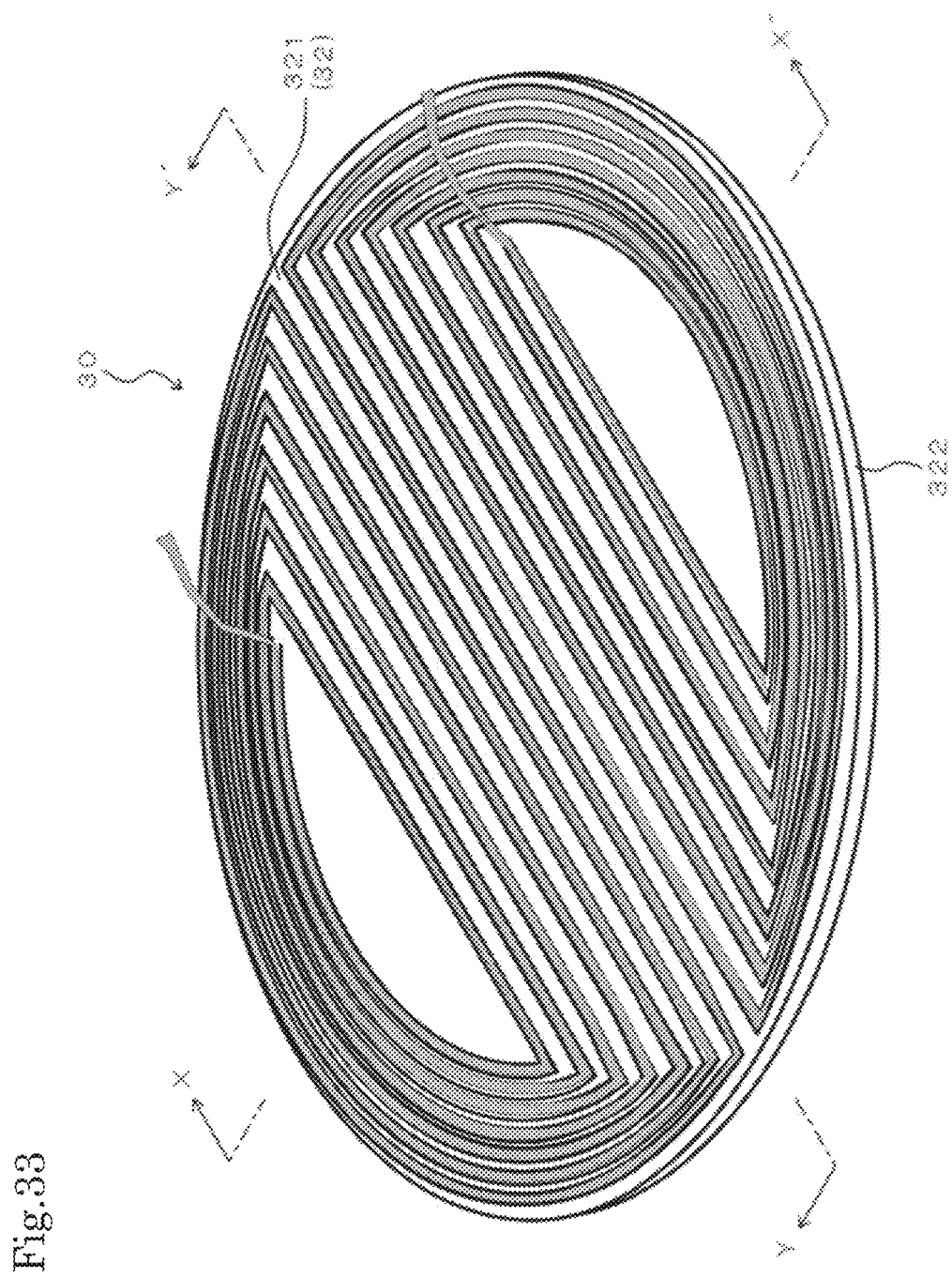
FIG. 33 is a schematic perspective view of an application part used in a magnetic stimulation device of a fourth embodiment of the present invention.
Figure 34:
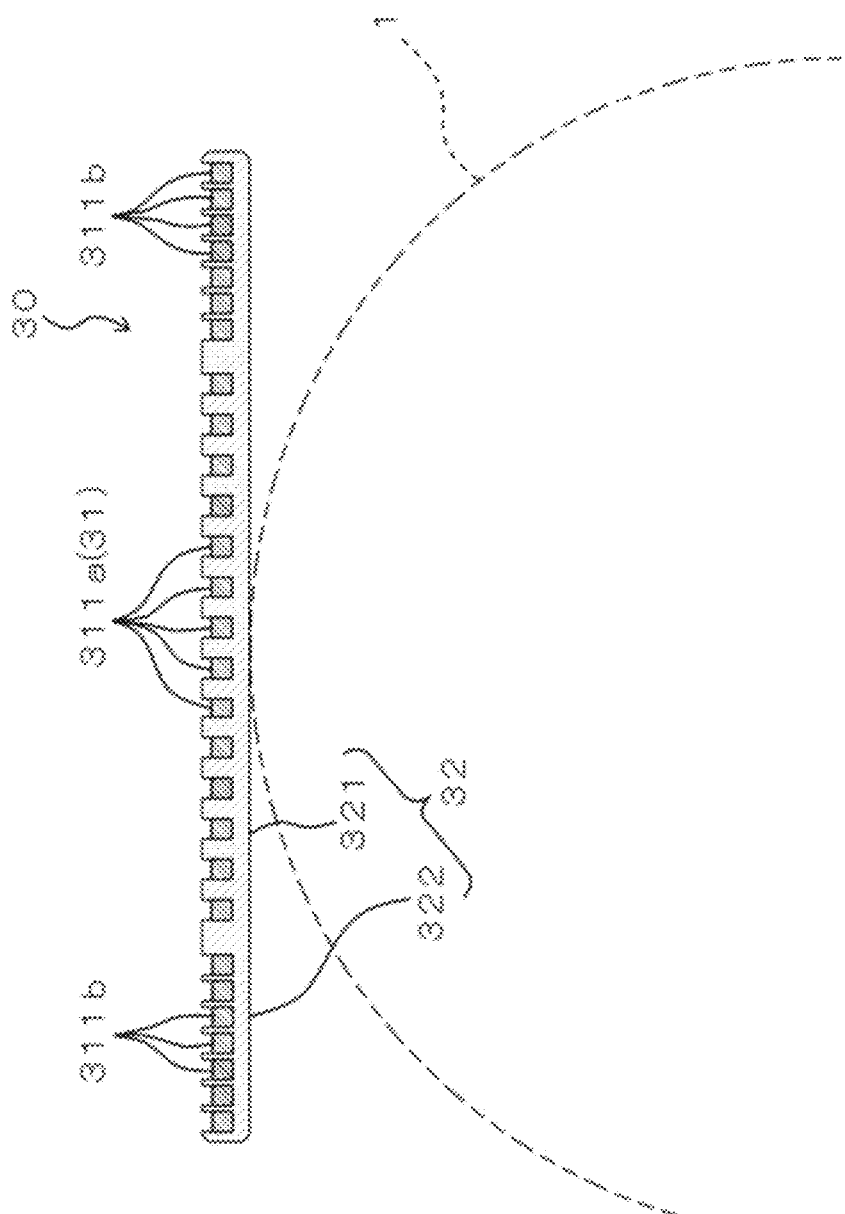
FIG. 34 is a horizontal cross sectional drawing taken along line X-X' in FIG. 33.
Figure 35:
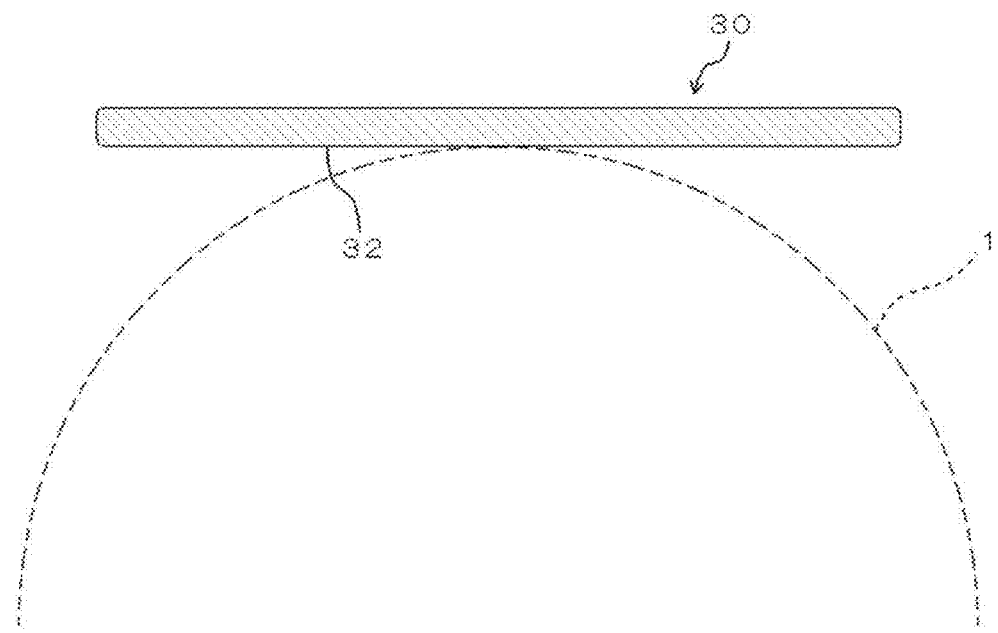
FIG. 35 is a vertical cross sectional drawing taken along line Y-Y' in FIG. 33.

Next, a magnetic stimulation device of a fourth embodiment of the present invention will be described with reference to FIG. 33 to FIG. 35. It should be noted that elements that are basically common to the magnetic stimulation device of the second embodiment that has already been described will be assigned the same reference numerals, to avoid duplicated description.

With the magnetic stimulation device of this embodiment, the flange section 322 is constructed extending from a peripheral edge of the contact section 321 in a direction that is the same as the extension direction of the contact section 321. In this way, with this embodiment, the whole of the support 32 is formed in a single disk shape.

Other structures and advantages of this fourth embodiment are the same as those of the previously described second embodiment, and so more detailed description has been omitted.

Practical Example 3

Simulation was carried out assuming the structure of the coil 31 of the previously described fourth embodiment. Simulation conditions were basically the same as those of the previously described practical example 1. However, with this practical example 3, in the following points,
object: hemispherical conductor of 100 mm radius
air region: radius 200 mm
conductivity of conduct constituting the coil: 0.106 S/m,
simulation conditions differed from those of previously described practical example 1.

Figure 36:
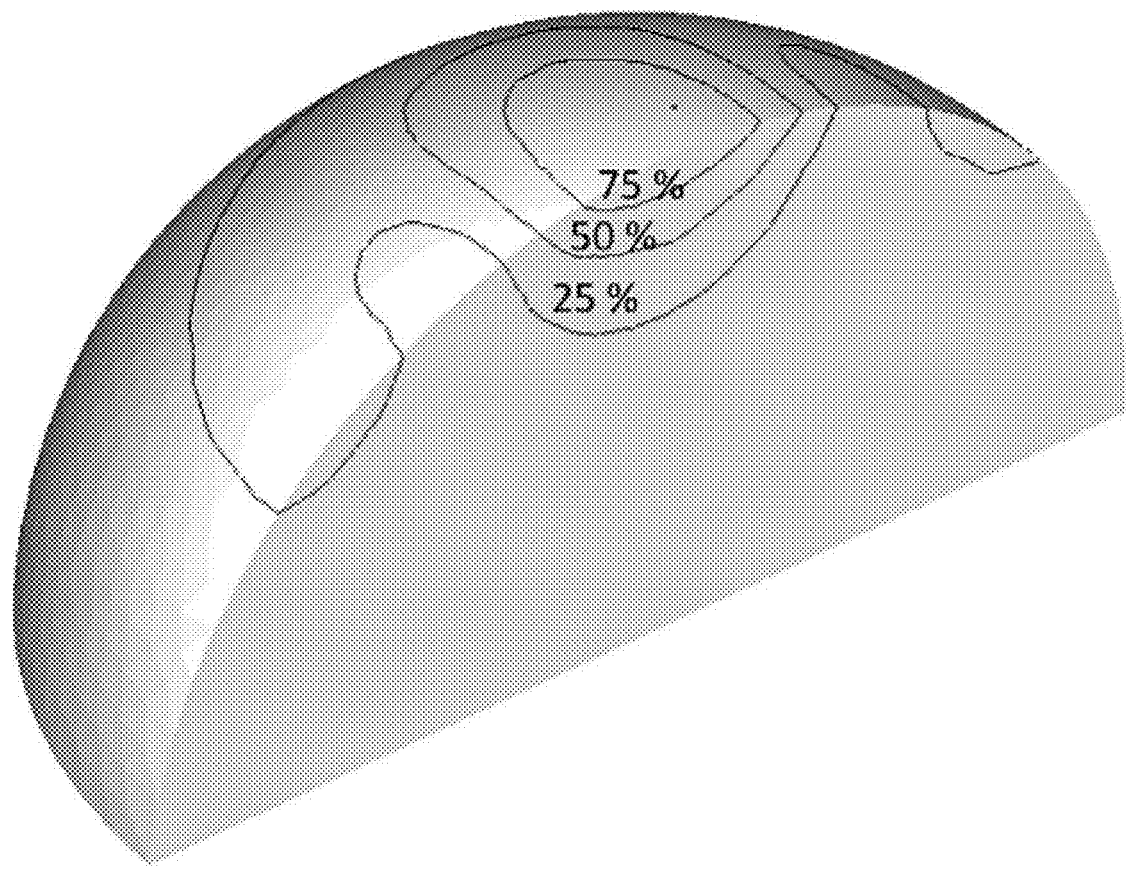
FIG. 36 is an explanatory drawing of results using simulation, and is an explanatory drawing showing electrical field intensity, generated by a coil of practical example 3, that has been normalized.
Figure 37:
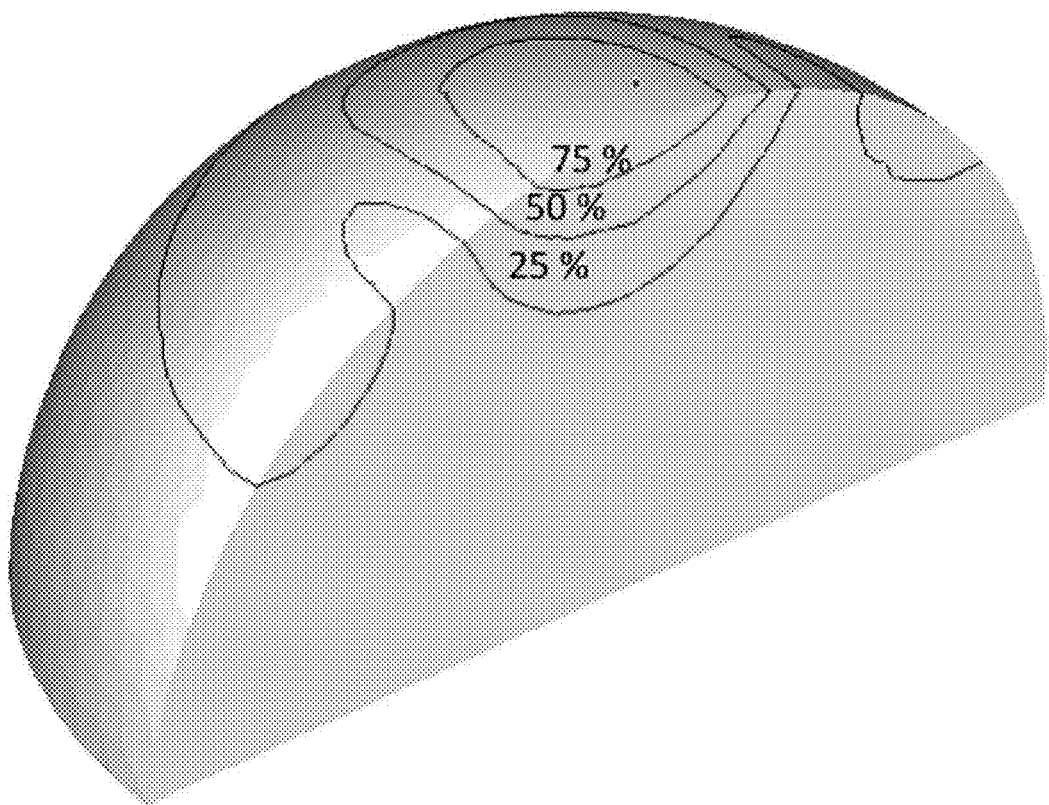
FIG. 37 is an explanatory drawing of results using simulation, and is an explanatory drawing showing electrical field intensity generated by a coil of practical example 1 that has been normalized, for the purpose of comparison with FIG. 36.
Figure 38:
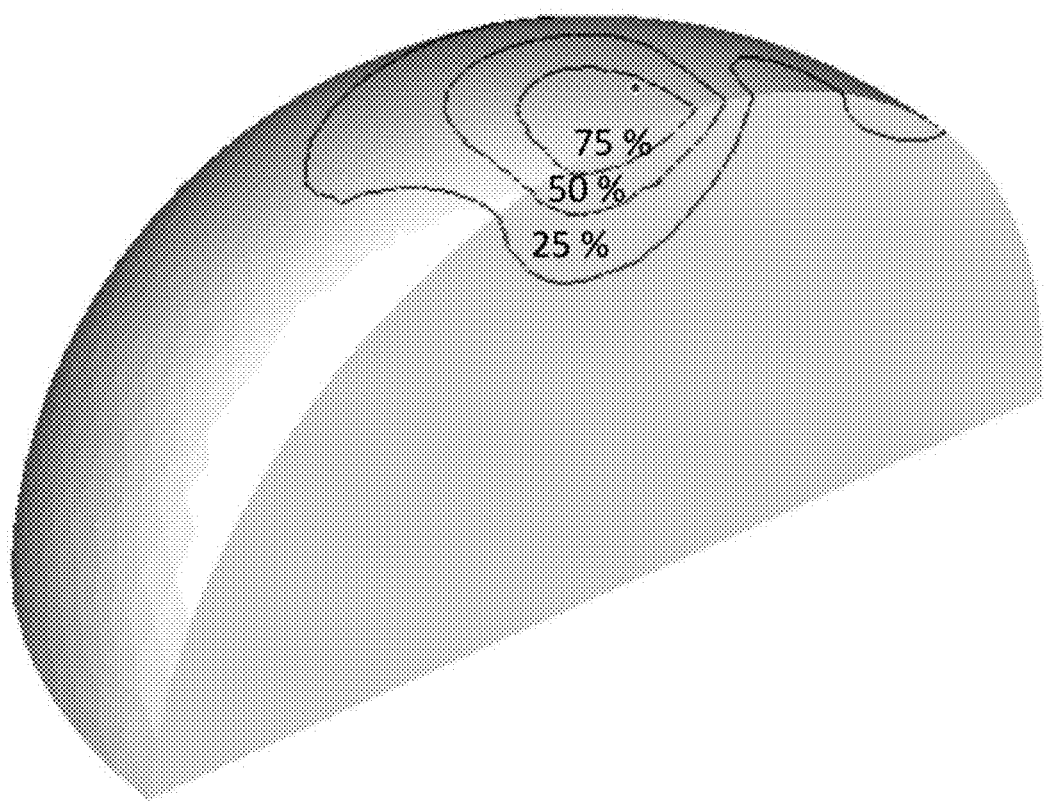
FIG. 38 is an explanatory drawing of results using simulation, and is an explanatory drawing showing electrical field intensity generated by a conventional figure 8 coil that has been normalized, for the purpose of comparison with FIG. 36.

Results are shown in table 5 below. In this table, the coil of practical example 3 is made "F-D coil". Also, for the purpose of comparison, results for the coil of practical example 1 are shown as "D-D coil" and results for the figure 8 coil constructed in the same way as the figure 8 coil of previously described table 3 are shown as "figure 8 coil". Further, electric field spreads for these coils, with the hemisphere model, are shown in FIG. 36 to FIG. 38.

TABLE 5

|  | FIG. 8 coil | D-D coil | F-D coil |
|---|---|---|---|
| Maximum Induced Electrical Field [V/m] | 230 | 277 | 181 |
| Inductance [µH] | 9.7 | 10.6 | 9.2 |
| Electrical Field Spread [cm] | 7.5 × 4.2 | 11.3 × 5.9 | 10.3 × 5.3 |

Figure 39:
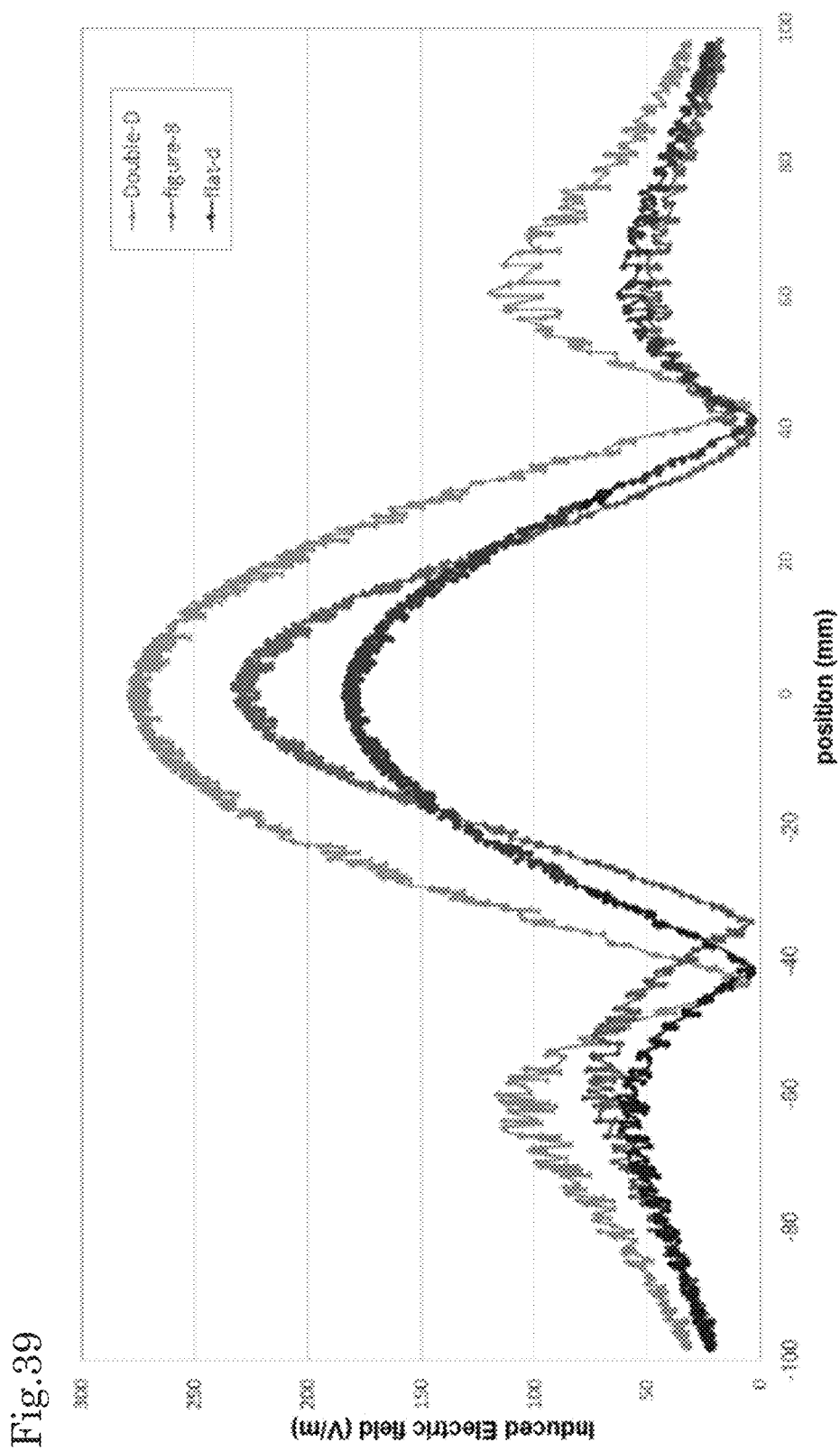
FIG. 39 is a graph for comparing a coil of practical example 3 (flat-d), a coil of practical example 1 (Double D) and a conventional figure 8 coil (FIG. 8), with the horizontal axis being measurement position (displacement from the coil center) and the vertical axis being induced electrical field intensity.

It should be noted that in this table 5, "electric field spread" means length of the center of an area in which ½ or more of a maximum electrical field intensity is induced. Further, for these coils, induced electrical wave distribution of a surface of the brain is shown in FIG. 39, and distribution of magnetic flux density in a depth direction is shown in FIG. 40.

From these results it will be understood that the F-D coil of practical example 3 has substantially the same electric field spread as the D-D coil of practical example 1. Further, it will be understood that at a depth position deeper than about 20 mm from the surface of the head (namely a contact point between the contact section 321 and the object 1), the F-D coil of practical example 3 has substantially the same magnetic flux density as the conventional figure 8 coil. Accordingly, according to the F-D coil of practical example 3, there is the advantage that it has the same robust characteristic as the coil of practical example 1, and it is possible to carry out magnetic stimulation to the same extent as with a conventional figure 8 coil.

It should be noted that the content of the present invention is not limited by each of the previously described embodiments. The present invention may additionally be subject to various changes to specific components, within a range disclosed in the scope of the patent claims.

For example, in each of the previously described embodiments, the head of a person has been described as an object, but the object can be made any appropriate living body (including an animal). It should be noted that in this specification the term animal is used with the meaning that includes human beings.

DESCRIPTION OF THE NUMERALS 1 object (head of a target person)
10 power supply section
20 cable
30 application part
31 coil
311 to 31N turn
311a actuation parts (actuation conductor sections)
311b connection parts (connection conductor sections)
32 support
321 contact section
321a groove on contract section
322 flange section
322a groove on flange section
33 core member
331 first portion
331a first core body
331b low magnetic permeability portion
332 second portion
332a second core body
332b low magnetic permeability portion
a interval between actuation part and connection part

What is claimed is:

1. A coil, adapted to be arranged close to an object, for causing an induced electrical field to be generated inside the object, the coil comprising:
a plurality of conductor turns comprising:
actuation parts arranged in parallel to each other, along a surface of the object or along another surface that is close to the surface of the object, for flow of an electrical current in one direction, and
connection parts arranged within a space in which the connection parts do not face the surface of the object over the actuation parts at a side of the coil, with respect to an extension direction of the actuation parts, for flow of the electrical current in a direction opposite to the one direction; and
a core member which is configured to reduce a magnetic resistance of a magnetic circuit that is generated by the plurality of conductor turns, and arranged at an opposite side to the object, over the actuation parts.

2. The coil of claim 1, wherein the connection parts of a first part of the plurality of conductor turns are arranged on the side of the coil that is opposite, with respect to the actuation parts, to another side of the coil where the connection parts of a second part of the plurality of conductor turns are arranged.

3. The coil of claim 1, wherein the connection parts are formed in a substantially arcuate shape.

4. The coil of claim 1, wherein the surface of the object or the another surface close to the surface of the object on which the actuation parts are arranged has a substantially arcuate cross section.

5. The coil of claim 1, wherein the actuation parts are arranged at equal intervals.

6. The coil of claim 1, wherein the object is a living body.

7. The coil of claim 1, wherein the object is a head of an animal, and
the coil is configured to produce induced current within a brain of the head as a result of the induced electrical field.

8. The coil of claim 1, wherein the core member has a plurality of regions of differing relative permeability.

9. The coil of claim 1, wherein the core member is provided with a first part that is arranged at a position that faces the actuation parts, and a second part that is arranged at a position facing the connection parts,
the first part is provided with a plurality of elongated first core bodies that extend in a direction that is not parallel to the extension direction of the actuation parts, and the second part is provided with a plurality of elongated second core bodies that extend in a direction that is substantially parallel to the extension direction of the actuation parts.

10. A magnetic stimulation device comprising the coil of claim 1, and a power supply configured to supply a predetermined electrical current to the coil.

11. A coil, adapted to be arranged close to a surface of an object, for causing an induced electrical field to be generated inside the object, the coil comprising:
   a core member, and
   a plurality of conductor turns which are formed to continuously extend from an input terminal of the coil to an output terminal of the coil,
   wherein the plurality of conductor turns comprises:
      (1) a plurality of actuation conductor parts used in generation of the induced electrical field, and
      (2) connection conductor parts that connect the plurality of actuation conductor parts together, and that are configured to minimize an effect of the connection conductor parts on an intensity of the induced electrical field generated by the plurality of actuation conductor parts,
   wherein the core member is configured to reduce magnetic resistance of a magnetic circuit generated by the plurality of conductor turns and arranged at an opposite side to the object over the plurality of actuation conductor parts.

12. A magnetic stimulation device comprising:
   a support;
   a coil, adapted to be arranged close to a surface of an object, for causing an induced electrical field to be generated inside the object, and comprising:
      a plurality of conductor turns comprising:
         actuation parts supported by the support and arranged substantially parallel to each other, for flow of an electrical current in one direction, and
         connection parts arranged in the coil laterally with respect to an extension direction of the actuation parts, for flow of the electrical current in a direction opposite to the one direction,
   wherein the support comprises:
      first grooves configured to accommodate the actuation parts and carry out an alignment of the actuation parts, and
      second grooves configured to accommodate the connection parts and carry out an alignment of the connection parts.

13. The magnetic stimulation device of claim 12, wherein the surface of the object is a substantially spherical shape, and
   a lower surface of the support has a center portion configured to contact the surface of the object.

* * * * *